US006951632B2

(12) United States Patent
Unger et al.

(10) Patent No.: US 6,951,632 B2
(45) Date of Patent: Oct. 4, 2005

(54) MICROFLUIDIC DEVICES FOR INTRODUCING AND DISPENSING FLUIDS FROM MICROFLUIDIC SYSTEMS

(75) Inventors: Marc A. Unger, South San Francisco, CA (US); Hou-Pu Chou, Sunnyvale, CA (US); Ian D. Manger, San Francisco, CA (US); Dave Fernandes, Pacifica, CA (US); Yong Yi, San Francisco, CA (US)

(73) Assignee: Fluidigm Corporation, South San Francisco, CA (US)

( * ) Notice: Subject to any disclaimer, the term of this patent is extended or adjusted under 35 U.S.C. 154(b) by 492 days.

(21) Appl. No.: 09/998,600

(22) Filed: Nov. 16, 2001

(65) Prior Publication Data

US 2002/0117517 A1 Aug. 29, 2002

Related U.S. Application Data

(60) Provisional application No. 60/249,230, filed on Nov. 16, 2000.

(51) Int. Cl.[7] ............................. B01L 3/02; B01L 11/00; B01L 3/00; B01L 9/00; G01N 15/06

(52) U.S. Cl. ........................ 422/100; 422/50; 422/55; 422/58; 422/68.1; 422/81; 422/82; 422/82.05; 422/101; 422/102; 422/103; 422/104; 436/43; 436/53; 436/54; 436/63; 251/129.01; 251/213; 137/1; 137/14; 204/193; 204/194; 435/283.1; 435/286.4; 435/286.5; 435/286.6; 435/287.1; 435/287.3

(58) Field of Search ............................. 422/50, 55, 58, 422/68.1, 81, 82, 82.05, 100–104; 436/43, 53, 54, 63; 251/129.01, 213; 137/1, 14; 204/193, 194; 435/283.1, 286.4, 286.5, 286.6, 287.1, 287.3

(56) References Cited

U.S. PATENT DOCUMENTS

| 3,570,515 A | 3/1971 | Kinner |
| 3,747,628 A | 7/1973 | Holster et al. |
| 4,046,159 A | 9/1977 | Pegourie |

(Continued)

FOREIGN PATENT DOCUMENTS

| EP | 0 592 094 A2 | 4/1994 |
| EP | 0 703 364 A1 | 3/1996 |
| EP | 0 706 004 A2 | 4/1996 |

(Continued)

OTHER PUBLICATIONS

Ahn et al., "Fluid Micropumps Based on Rotary Magnetic Actuators," Proceedings of 1995 IEEE Micro Electro Mechanical Systems Workshop (MEMS '95), held in Amsterdam, Netherlands on Jan. 29–Feb. 2, 1995, pp. 408–412.

Benard et al., "A Titanium–Nickel Shape–Memory Alloy Actuated Micropump," Proceedings of Transducers '97, 1997 International Conference on Solid–State Sensors and Actuators, held in Chicago, IL., Jun. 16–19, 1997, 1:361–364 (1997).

Brechtel et al.; "Control of the electrosmotic flow by metal–salt–containing buffers", J Chromatography A, 1995, pp. 97–105, vol. 716.

(Continued)

Primary Examiner—Jill Warden
Assistant Examiner—Brian J. Sines
(74) Attorney, Agent, or Firm—Townsend and Townsend Crew LLP

(57) ABSTRACT

The present invention provides microfluidic devices, systems and methods for using the same, which facilitate the introduction of fluid to and from a microfluidic channel located within the microfluidic devices.

2 Claims, 19 Drawing Sheets

U.S. PATENT DOCUMENTS

| | | | |
|---|---|---|---|
| 4,119,368 | A | 10/1978 | Yamakazi |
| 4,153,855 | A | 5/1979 | Feingold |
| 4,245,673 | A | 1/1981 | Bouteille et al. |
| 4,434,704 | A | 3/1984 | Surjaatmadja |
| 4,898,582 | A | 2/1990 | Faste |
| 5,085,562 | A | 2/1992 | van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki |
| 5,178,190 | A | 1/1993 | Mettner |
| 5,224,843 | A | 7/1993 | Van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,304,487 | A * | 4/1994 | Wilding et al. ............... 435/29 |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom |
| 5,400,741 | A | 3/1995 | DeTitta et al. |
| 5,423,287 | A | 6/1995 | Usami et al. |
| 5,529,465 | A | 6/1996 | Zengerle et al. |
| 5,593,130 | A | 1/1997 | Hansson et al. |
| 5,642,015 | A | 6/1997 | Whitehead et al. |
| 5,659,171 | A | 8/1997 | Young et al. |
| 5,660,370 | A | 8/1997 | Webster |
| 5,681,024 | A | 10/1997 | Lisec et al. |
| 5,705,018 | A | 1/1998 | Hartley |
| 5,743,960 | A | 4/1998 | Tisone |
| 5,759,014 | A | 6/1998 | Van Lintel |
| 5,775,371 | A | 7/1998 | Pan et al. |
| 5,836,750 | A | 11/1998 | Cabuz |
| 5,842,787 | A | 12/1998 | Kopf-Sill et al. |
| 5,846,396 | A | 12/1998 | Zanzucchi et al. |
| 5,872,010 | A | 2/1999 | Karger et al. |
| 5,875,817 | A | 3/1999 | Carter |
| 5,876,187 | A | 3/1999 | Forster et al. |
| 5,879,632 | A | 3/1999 | Demers |
| 5,885,470 | A * | 3/1999 | Parce et al. .................... 216/33 |
| 5,932,799 | A | 8/1999 | Moles |
| 5,942,443 | A | 8/1999 | Parce et al. |
| 6,007,309 | A | 12/1999 | Hartley |
| 6,033,544 | A | 3/2000 | Demers et al. |
| 6,033,546 | A | 3/2000 | Ramsey |
| 6,043,080 | A | 3/2000 | Lipshutz et al. |
| 6,068,751 | A | 5/2000 | Neukermans |
| 6,086,825 | A | 7/2000 | Sundberg et al. |
| 6,090,251 | A | 7/2000 | Sundberg et al. |
| 6,117,396 | A | 9/2000 | Demers |
| 6,123,769 | A | 9/2000 | Sanjoh |
| 6,155,282 | A | 12/2000 | Zachary et al. |
| 6,174,365 | B1 | 1/2001 | Sanjoh |
| 6,176,962 | B1 * | 1/2001 | Soane et al. ................ 156/292 |
| 6,296,673 | B1 | 10/2001 | Santarsiero et al. |
| 6,391,622 | B1 * | 5/2002 | Knapp et al. ............ 435/285.2 |
| 6,408,878 | B2 * | 6/2002 | Unger et al. ................ 137/597 |
| 6,409,832 | B2 | 6/2002 | Weigl et al. |
| 6,720,710 | B1 * | 4/2004 | Wenzel et al. .............. 310/328 |

FOREIGN PATENT DOCUMENTS

| | | |
|---|---|---|
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 98/07069 A1 | 2/1998 |
| WO | WO 99/17093 A1 | 4/1999 |
| WO | WO 00/60345 A1 | 10/2000 |
| WO | WO 02/060582 A2 | 8/2002 |

OTHER PUBLICATIONS

Bryzek et al.; "Micromachines on the March", IEEE Spectrum, 1994, pp. 20–31, vol. 31, No. 5.

Buchaillot et al.; "Silicon nitride thin films Young's modulus determination by an optical non–destructive method", Jpn. J Appl Phys, 1995, pp. L794–L797, vol. 36, No. 2:6B.

Chiu et al.; "Patterned Deposition of Cells and Proteins onto Surfaces by Using Three–Dimensional Microfluidic Systems", Proc. Natl. Acad. Sci., 2000, pp. 2408–2413, vol. 97, No. 6.

Chou et al. "A microfabricated device for sizing and sorting DNA molecules", Applied Physical Sciences, Biophysics, Proc. Natl. Acad. Sci., 1999, pp. 11–13, vol. 96, U.S.A.

Delamarche et al.; "Patterned delivery of immunoglobulins to surfaces using microfluidic networks", Science, 1997, pp. 779–781, vol. 276.

Duffy et al. "Patterning Electroluminescence Materials with Feature Sizes as Small as 5$\mu$m Using Elastomeric Membranes as Masks for Dry Lift–Off", Advanced Materials, 1999, pp. 546–552, vol. 11, No. 7.

Duffy et al. "Rapid Prototyping of Microfluidic Switches in Poly(dimethylsiloxane) and Their Actuation by Electro–Osmotic Flow" Journal of Microeng, 1999, pp. 211–217, vol. 9.

Duffy et al. "Rapid Prototyping of Microfluidic Systems in Poly(dimethylsiloxane)", Analytical Chemistry, 1998, pp. 4974–4984, vol. 70, No. 23.

Effenhauser et al.; "Integrated capillary electrophoresis on flexible silicone microdevices: Analysis of DNA restriction fragments and detection of single DNA molecules on microchips", Anal. Chem, 1997, pp. 3451–3457, vol. 69.

Effenhauser et al.; "Integrated chip–based capillary electrophoresis", Electrophoresis, 1997, pp. 2203–2213, vol. 18.

Fahrenberg et al. "A microvalve system fabricated by thermoplastic molding", J Micromech Microeng, 1995, pp. 169–171, vol. 5.

Fu et al.; "A microfabricated fluorescence–activated cell–sorter", Nature Biotechnology, 1999, pp. 1109–1111, vol. 17.

Gass et al., "Integrated flow–regulated silicon micropump," Sensors and Actuators A Physical, 1994, p. 335–338, vol. 43.

Gerlach, T., "Pumping Gases by a Silicon Micro Pump with Dynamic Passive Valves," Proceedings of Transducers '97, 1997 International Conference on Solid–State Sensors and Actuators, held in Chicago, Il., Jun. 16–19, 1997, pp. 357–360, vol. 1.

Goll et al., "Microvalves with bistable buckled polymer diaphragms," J. Micromech. Microeng., 1996, pp. 77–79, vol. 6.

Gravesen et al.; "Microfluids—A Review", Journal Micromech Microeng, 1993, pp. 168–192, vol. 3.

Harrison et al., "Micromachining a Miniaturized Capillary Electrophoresis–Based Chemical Analysis System on a Chip," Science, 1993, pp. 895–897, vol. 261.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15–17, 1988, Optical Society of America, pp. 107–110.

Hosokawa et al., "Handling of Picoliter Liquid Samples in a Poly(dimethylsiloxane)-Based Microfluid Device," Anal. Chem., 1999, 71(20):4781–4785.

Ikuta et al., "Three dimensional micro integrated fluid systems (MIFS) fabricated by stereo lithography," IEEE Kyushu Institute of Technology, 1994, pp. 1–6.

Jacobson et al., "High–speed separations on a microchip," Anal. Chem., 1994, 66(7):1114–1118.

Jacobson et al., "Microfluidic Devices for Electrokinetically Driven Parallel and Serial Mixing," Anal. Chem., 1999, 71(20):4455–4459.

Jerman, H., "Electrically–Activated, Normally–Closed Diaphragm Valves," Proceedings of Transducers '91, 1991 International Conference on Solid–State Sensors and Actuators, pp. 1045–1048 (1991).

Jung et al., "Chemical and Physical Interactions at Metal/Self–Assembled Organic Monolayer Interfaces," Critical Reviews in Solid State and Material Sciences, 1994, pp. 2–10, vol. 19, No. 1.

Kenis et al. "Microfabrication Inside Capillaries Using Multiphase Laminar Flow Patterning," Science, 1999, 285:83–85.

Kim, Enoch et al., "Micromolding in Capillaries: Applications in Material Science," J. American Chemical Society, 118:5722–5731 (1996).

Kopp et al. "Chemical Amplification: Continuous–Flow PCR on a Chip", Science, 1998, 280:1046–1048.

Kuhn et al. "Silicon Charge Electrode Array for Ink Jet Printing", IEEE Transactions on Electron Devices, 1978, pp. 1257–1260, vol. ED–25, No. 10.

Lin et al. "Free–Space Micromachined Optical Switches for Optical Networking," IEEE J. Selected Topics in Quantum Electronics, 1999, pp. 4–9, vol. 5, No. 1.

Lötters et al. "The mechanical properties of the rubber elastic polymer polydimethylsiloxane for sensor applications," J. Micromech. Microeng., 1997, 7:145–147.

Lucy et al., "Characterization of the Cationic Surfactant Induced Reversal of Electroosmotic Flow in Capillary Electrophoresis," Anal. Chem., 1996, pp. 300–305, vol. 68.

Maluf, N., An Introduction to Microelectromechanical Systems Engineering, Artech House Publishers, Boston London pp. 42–45.

Muller et al., "Surface–Micromachined Microoptical Elements and Systems," Proceedings of IEEE, 1998, 86(8):1705–1720.

Olsson et al., "Simulation Studies of Diffuser and Nozzle Elements for Valve–less Micropumps," Proceedings of Transducers '97, 1997 International Conference on Solid–State Sensors and Actuators, held in Chicago, Il., Jun. 16–19, 1997, 2:1039–1042 (1997).

Markx et al. "Applications of dielectrophoresis in biotechnology," Tibtech, 15:426–432 (1997).

Qin et al., "Photolithography with transparent reflective photomasks," J. Vac.Sci. Technology, 16(1):98–103 (1998).

Qin et al., "Elastomeric Light Valves**", Adv. Mater., 1997, pp. 407–410, vol. 9, No. 5.

Quake S.R. and Scherer A.; "From Micro– to Nanofacrication with Soft Materials", Science, Nov. 24, 2000; pp. 1536–1540, vol. 290, No. 5496.

Rapp. R., "LIGA micropump for gases and liquids," Sensors and Actuators A, 1994, pp. 57–61, vol. 40.

Roylance et al., "A Batch–Fabricated Silicon Accelerometer", IEEE Transactions on Electron Devices, Dec. 1979, pp. 1911–1917, vol. ED–26, No. 12.

Schasfoort et al., "Field–Effect Flow Control for Microfabricated Fluidic Networks," Science, 1999, 286:942–945.

Schueller et al., "Fabrication of glassy carbon microstructures by soft lithography," Sensors and Actuators, 72(2):125–139 (1999).

Shoji et al.; "Smallest Dead Volume Microvalves for Integrated Chemical Analyzing Systems", Proceedings of Transducers '91, 1991, pp. 1052–1055, San Francisco.

Shoji, S., "Fluids for Sensors Systems", Topics in Current Chemistry, 1998, pp. 162–188, vol. 194, Springer Verlag Berlin Heidelberg.

Smits, J.G., "Piezoelectric Micropump with Three Valves Working Peristaltically", Sensors and Actuators, 1990, pp. 203–206, vol. A21–A23.

Sohn et al., "Capacitance cytometry: Measuring biological cells one by one," PNAS, 97(20):10687–10690 (2000).

Tufte et al., "Silicon Diffused–Element Piezoresistive Diaphragms," J. Appl. Phys., Nov. 1962, pp. 3322–3327, vol. 33, No. 11.

Ullmann's Encyclopedia of Industrial Chemistry, Sections 6 to 6.3, Topic: Carbon Black, Sixth Edition, 1999.

Unger, Marc A. et al. "Monolithic Microfabricated Valves and Pumps by Multilayer Soft Lithography" Science, Apr. 7, 2000, vol. 288, 113–116.

Van de Pol et al., "Micro Liquid Handling Devices—A Review", Micro Systems Technologies, 1990, pp. 799–805, vol. 90.

Van de Pol, F.C.M. et al. "A Thermo–Pneumatic Actuation Principle for a Microminiature Pump and Other Micromechanical Devices" Sensors and Actuators, May 3, 1989, pp. 139–143, vol. 17, Nos. 1–2.

Vieider et al.; "A Pneumatically Actuated Micro Valve with a Silicon Rubber Membrane for Integration with Fluid Handling Systems", Proceedings of Transducers '95, the 8th International Conference on Solid–State Sensors and Actuators and Eurosensors IX, held in Stockholm, Sweden on Jun. 25–29, 1995, 1995, pp. 284–286, Stockholm, Sweden.

Washizu et al., "Molecular Dielectrophoresis of Biopolymers," IEEE Transactions on Industry Applications, 1994, 30(4):835–843.

Xia et al., "Complex Optical Surfaces Formed by Replica Molding Against Elastomeric Masters," Science, 1996, 273:347–349.

Xia et al., "Soft Lithography," Angew. Chem. Int. Ed., 1998, 37:551–575.

Xia, Y. et al., "Micromolding of Polymers in Capillaries: Applications in Microfabrication," Chemistry of Materials, 8(7):1558–1567 (1996).

Yang et al. "A Mems Thermopneumatic Silicone Membrane Valve", Proceedings of IEEE, 10th Annual International Workshop on MicroElectro Mechanical Systems, Sensors and Actuators, 1998, A64(1):101–108.

Yang et al., "A MEMS Thermopneumatic silicone Membrane Valve," Proceedings of the IEEE 10th Annual Workshop of Micro Electro Mechanical Systems Workshop (MEMS '97), held Jan. 26–30, 1997 in Nagoya, Japan, pp. 114–118.

Yazdi et al. "Micromachined Intertial Sensors," Proceedings of IEEE, 1998, 86(8):1640–1659.

Young et al. "Contoured elastic–membrane microvalves for microfluidic network integration," J. Biomechanical Engineering, 1999, 121:2–6.

Zengerle et al., "A Micro Membrane Pump with Electrostatic Actuation," 1992 IEEE Conf. on Micro Electro Mechanical Systems, held Feb. 4–7, 1992 in Travemunde Germany, pp. 19–24.

Zengerle et al., "Performance Simulation of Microminiaturized Membrane Pumps," from 7th International Conference on Solid–State Sensors and Actuators held Jun. 7–10, 1993 in Yokohama Japan, pp. 106–109.

* cited by examiner

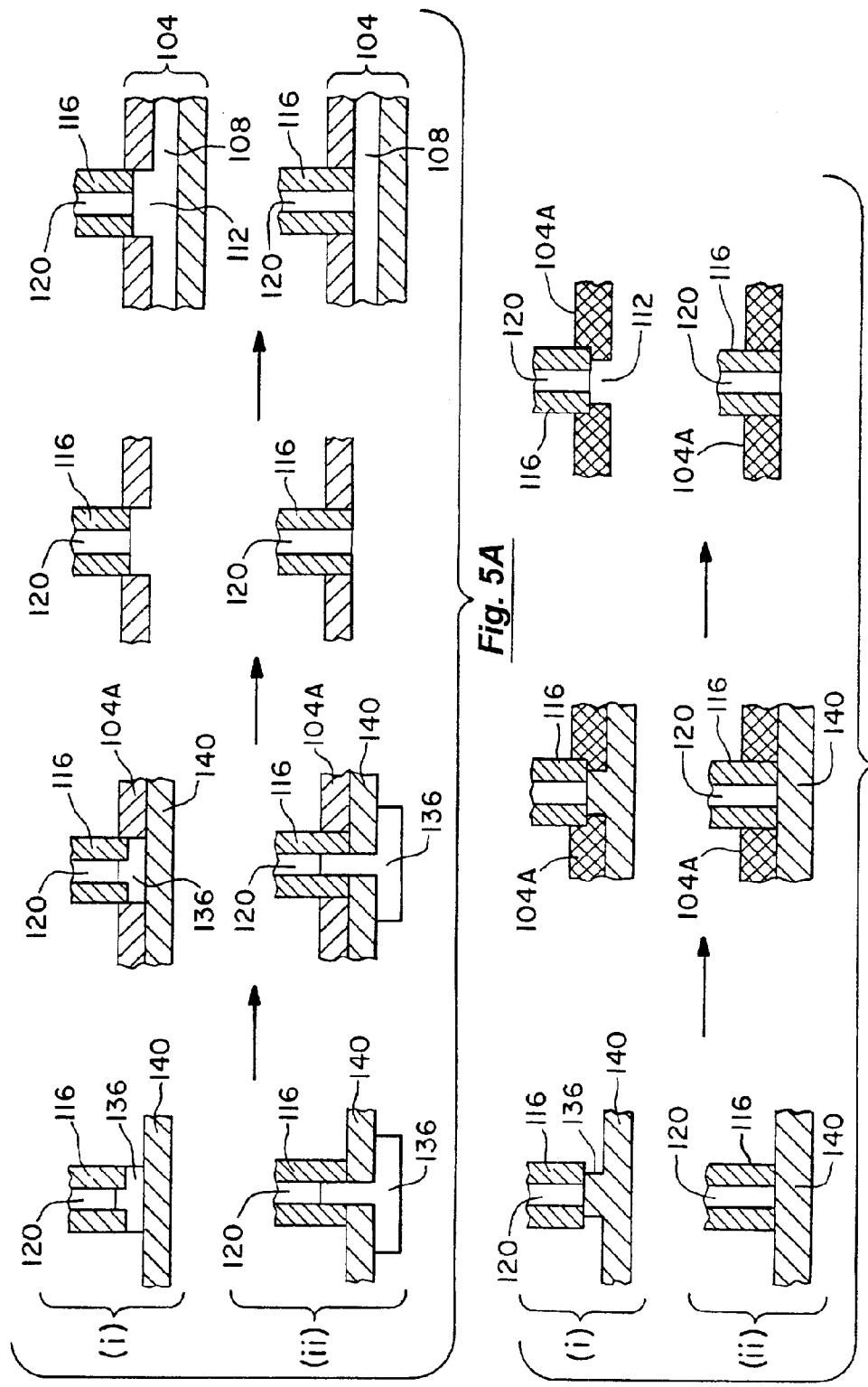

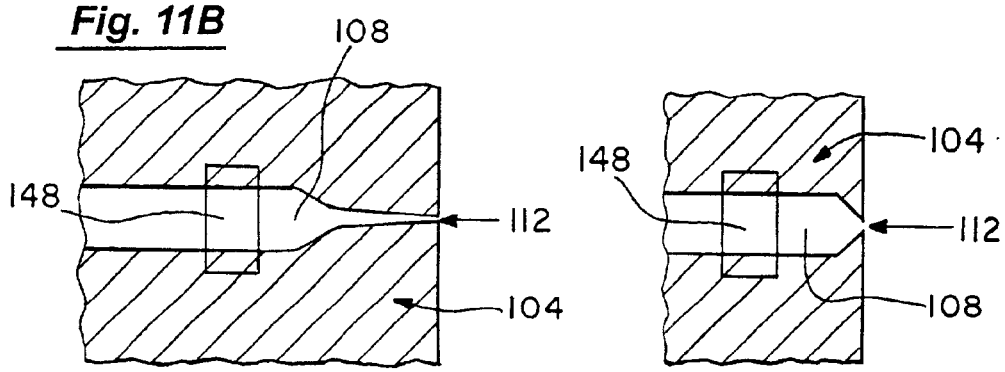
Fig. 11B
Fig. 11C
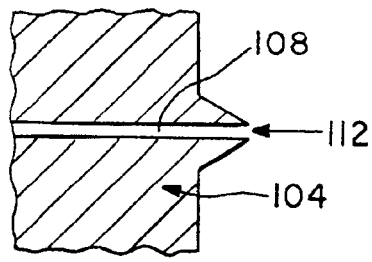
Fig. 11A
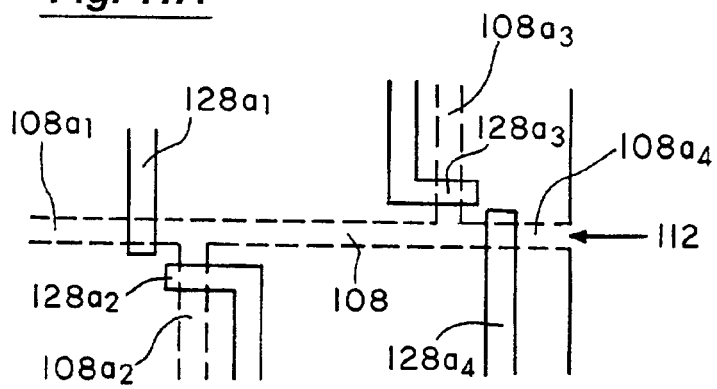
Fig. 12A
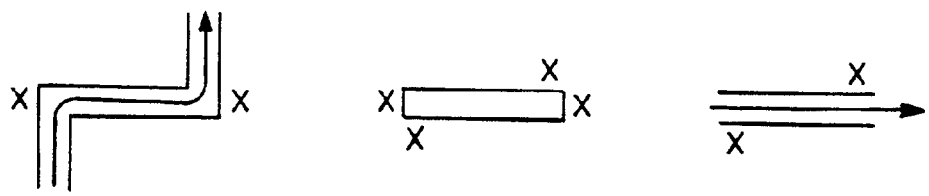
Fig. 12B    Fig. 12C    Fig. 12D

MICROFLUIDIC DEVICES FOR INTRODUCING AND DISPENSING FLUIDS FROM MICROFLUIDIC SYSTEMS

CROSS REFERENCE TO RELATED APPLICATIONS

This application claims priority benefits of U.S. Provisional Patent Application Ser. No. 60/249,230, filed Nov. 16, 2000, which is incorporated herein by reference in its entirety.

FIELD OF THE INVENTION

The present invention relates generally to microfluidic devices and systems and methods for using the same. More particularly, the present invention provides structures and methods which facilitate the introduction and dispensing of fluids to and from devices having microfluidic channels.

BACKGROUND OF THE INVENTION

There are variety of microfluidic devices which are useful in a variety of applications, including for performing chemical, clinical, and environmental analysis of chemical and biological samples. Microfluidic devices are often fabricated using photolithography, wet chemical etching, and other techniques similar to those employed in the semiconductor industry. The resulting devices can be used to perform a variety of sophisticated chemical and biological synthetic and analytical techniques.

Microfluidic devices are particularly well suited for microscale chemical synthesis and analysis of minute quantities of samples. The amount of sample required is typically on the order of nanoliters and even picoliters. Microfluidic devices can be produced at relatively low cost, and the channels can be arranged to perform numerous specific analytical or synthetic operations, including mixing, dispensing, valving (i.e., controlling the flow of samples), detecting, conducting electrophoresis, and the like. The synthetic and analytical capabilities of microfluidic devices are generally enhanced by increasing the number and complexity of network channels, reaction chambers, and the like.

Unfortunately, the structures and methods used to introduce samples and other fluids into microfluidic devices can limit their capabilities. Fluid introduction ports (i.e., orifices or fluid inlets/outlets) provide an interface between the surrounding world and the microfluidic channel network. Current structures and methods for transporting fluids to and from microfluidic devices generally result in the transfer of a much greater volume of fluid than is needed for microfluidic synthesis or analysis.

Recently, microfluidic devices fabricated from elastic materials have been developed providing a variety of sample manipulations within the microfluidic devices, thereby significantly increasing the utility of microfluidic devices. For example, such microfluidic devices have been demonstrated to be useful in combinatorial synthesis, and sorting minute particles, cells, oligonucleotides, peptides, and other detectable molecules. However, one problem that remains is introduction of samples into the microfluidic devices. Although the capacity of most microfluidic devices is in the order of nanoliters or picoliters, typically a sample on the order of microliters is required for transfer into microfluidic devices. This relatively large quantity of sample needed negates one of the primary advantages of using microfluidic devices in sample analysis and synthesis.

Similarly, there have been few methods developed for transferring small quantities of sample from microfluidic devices to conventional fluid handling systems. One of the primary method uses electroosmotic forces which requires ionic solutions to transport fluids to and from or within the microfluidic channel. This requirement of having ionic solution to transport a fluid medium also severely limits the applicability of microfluidic devices.

Therefore there is a need for microfluidic devices or systems which facilitate the transfer of small volumes (i.e., in the order of less than about 1 $\mu$L, and preferably less than 0.1 $\mu$L) of samples or fluids to and from the microfluidic devices. There is also a need to increase the number of fluids which can be manipulated within the microfluidic device without increasing the overall size of the microfluidic device itself. There is also a need for providing a means for filling or dispensing a predetermined amount of samples or fluids to and from the microfluidic channels.

SUMMARY OF THE INVENTION

One aspect of the present invention provides a microfluidic device comprising:

a body structure comprising an elastomeric polymer substrate;

a microfluidic channel disposed within said elastomeric polymer substrate;

a port on a surface of said body structure and in fluid communication with said microfluidic channel for introducing or dispensing a fluid to or from said microfluidic channel; and a means for transporting the fluid to and from said microfluidic channel.

Preferably, the elastomeric polymer substrate has a Young's modulus of about 3 MPa or less.

In one embodiment, the microfluidic device further comprises at least one valve system which comprises:

a control channel disposed within said elastomeric polymer substrate; and one or more valves operatively connected to said microfluidic channel to regulate fluid flow through said microfluidic channel, wherein each of said valves comprises a portion of said elastomeric polymer substrate that is located between said control channel and said microfluidic channel, and wherein each of said valves is capable of being deflected into or retractable from said microfluidic channel upon which said valve operates in response to an actuation force applied to said control channel, said valve when positioned in said microfluidic channel is capable of affecting fluid flow therethrough.

In one particular embodiment, a pair of valve systems is operatively disposed with respect to one another such that when the each valve of the pair of valve system extends into the microfluidic channel a holding space is formed between the valves in which the fluid can be retained. In this manner, a specific volume of fluid can be retained within and/or dispensed from the microfluidic channel.

Yet in another embodiment, the means for transporting the fluid comprises a fluid pump comprising at least one of said valve system. In conventional fluid sampling using a microfluidic device, it is difficult to initially sample a liquid into a dry microfluidic channel. Typically, the microfluidic channel is primed, i.e., washed with the liquid sample, prior to actually sampling the liquid. It has been found be present inventors that when the valve system disclosed herein is used as the fluid pump, a liquid can be sampled into a dry microfluidic channel without the need for priming or wetting the microfluidic channel. Thus, in one embodiment, the microfluidic channel is dry prior to sampling a liquid.

In one specific embodiment, the fluid pump comprises a single control channel. In this embodiment, the fluid pump can comprise one valve and the tip of the fluid pump control channel can be tapered. Tapered fluid pump control channel allows a substantially complete actuation of the valve. In another embodiment, the fluid pump control channel further comprises at least one capacitor which is capable of delaying actuation of said control channel. In another particular embodiment, the fluid pump comprises a plurality of valves described above. In this embodiment, the control channel of fluid pump can be interdispersed with at least one normally closed valve system. In yet another embodiment, the control channel of fluid pump is interdispersed with at least one constricted region.

In another embodiment, the single line pump forms a pump having two more valve locations separated by channel sections of smaller cross section. This constriction causes a delay in the filling of the subsequent sections.

Yet in another embodiment, the fluid pump comprises a plurality of the valve systems. Typically, each valve system can be actuated independently of the other. And by actuating each valve system in a sequence, a peristaltic action can be created within the microfluidic channel.

Preferably, the fluid pump is capable of dispensing nanoliter volumes with high precision (e.g., <5% error). In one particular embodiment, the fluid pump is capable of providing a relatively constant fluid flow rate in the order of $\mu L/min$ scale or less.

The control channel can be actuated by a variety of methods known to one of ordinary skill in the art. In one particular embodiment, the valve system is actuated by pneumatic, electrostatic, piezoelectric, thermal or magnetic means. Preferably, the control channel is actuated by pneumatic means.

Still yet in another embodiment, the microfluidic device comprises a plurality of valve systems described herein. In particular, at least one of the valve system is capable of affecting the fluid flow direction. In this manner, back flow of the fluid can be avoided or substantially minimized by deflecting one of the valves into the microfluidic channel prior to activating the pump system.

Yet in another embodiment, the microfluidic channel is an integrated microfluidic channel comprising at least first and second intersecting microscale fluidic channels, wherein the first microscale fluidic channel is in fluid communication with the port. This allows a variety of fluid manipulations within the microfluidic channel.

In yet another embodiment, the body structure further comprises an elongated capillary protuberance, wherein the port is disposed on or near the tip of the elongated capillary protuberance. This elongated capillary protuberance provides an easy fluid sampling means. In one specific embodiment, the microfluidic device comprises a plurality of such elongated capillary protuberances, each having a port that is disposed on or near its tip. Instead of elongated capillary protuberances, the microfluidic device of the present invention can further comprise a capillary element comprising a capillary channel disposed therethrough. In such embodiment, one end of the capillary element is inserted into the port and positioned such that the capillary channel is in fluid communication with the microfluidic channel. In addition, when the microfluidic device comprises a plurality of ports, each port can comprise a capillary element. In either instances, presence of a plurality of ports allows sampling of a large number of fluids using a single microfluidic device.

When a capillary element is attached to the body structure, preferably the diameter of the port is substantially greater than the diameter of the microfluidic channel. This allows the capillary element to be easily inserted into the port. The capillary element can be removably attached to the elastomeric polymer substrate.

Still in another embodiment, the microfluidic channel is tapered towards the port. This tapering near the port or the fluid outlet provides a jet-spray like fluid dispensing system.

In still another embodiment, the body structure comprises a plurality of ports.

Yet in another embodiment, the body structure further comprises a passageway defining an interstitial surface and which extends from a first surface to a second surface of said body structure; and wherein said port is disposed within said interstitial surface.

Still in another embodiment, the means for transporting the fluid comprises a vacuum device attached to a second port located within said body structure and which is in fluid communication with said microfluidic channel, whereby operation of said vacuum device introduces the fluid into the microfluidic channel through the port.

Yet still in another embodiment, the microfluidic channel further comprises a narrow section that is capable of preventing further introduction of the fluid into said microfluidic channel when the fluid reaches said narrow section.

Another aspect of the present invention provides a microfluidic device comprising:

(a) a body structure comprising an elastomeric polymer substrate;

(b) a microfluidic channel disposed within said elastomeric polymer substrate;

(c) a fluid inlet in fluid communication with said microfluidic channel; and (d) a fluid pump for introducing or dispensing a fluid to or from said microfluidic channel through said port, wherein said fluid pump comprises:

(i) a fluid pump control channel disposed within said elastomeric polymer substrate; and (ii) one or more pump valves operatively connected to said microfluidic channel to regulate fluid flow through said microfluidic channel, wherein each of said pump valves comprises a portion of said elastomeric polymer substrate that is located between said fluid pump control channel and said microfluidic channel, and wherein each of said pump valves is capable of being deflected into or retractable from said microfluidic channel upon which said fluid pump valve operates in response to an actuation force applied to said fluid pump control channel, said fluid pump valve when positioned in said microfluidic channel is capable of affecting fluid flow therethrough.

In one particular embodiment, the microfluidic device further comprises a control valve system which comprises:

a control channel disposed within said elastomeric polymer substrate; and a control valve operatively connected to said microfluidic channel to regulate fluid flow through said microfluidic channel, wherein said control valve comprises a portion of said elastomeric polymer substrate that is located between said control channel and said microfluidic channel, and wherein said valve is capable of being deflected into or retractable from said microfluidic channel upon which said valve operates in response to an actuation force applied to said control channel, said valve when positioned in said microfluidic channel is capable of restricting fluid flow therethrough.

Yet in another embodiment, the fluid pump comprises one fluid pump channel. The fluid pump channel can comprise a plurality of capacitors which are capable of delaying actuation of said fluid pump control channel.

In another embodiment, the fluid pump comprises a plurality of said fluid pump channels.

In yet another embodiment, the fluid inlet comprises an elongated capillary protuberance having a capillary channel disposed therethrough, wherein said capillary channel is in fluid communication with said microfluidic channel.

Still in another embodiment, the fluid inlet comprises a capillary element comprising a capillary channel disposed therethrough, wherein said capillary channel is in fluid communication with said microfluidic channel.

Another aspect of the present invention provides a method for sampling a fluid comprising:
(a) providing a microfluidic device which comprises:
(i) a body structure comprising an elastomeric polymer substrate;
(ii) a microfluidic channel disposed within said elastomeric polymer substrate;
(iii) a fluid inlet in fluid communication with the microfluidic channel for introducing a fluid into the microfluidic channel; and
(iv) a means for introducing the fluid sample into the microfluidic channel,
(b) contacting the fluid inlet with the fluid sample; and
(c) introducing at least a portion of the fluid sample into the microfluidic channel using the fluid introducing means.

In one embodiment, the microfluidic device further comprises at least one valve system, wherein each valve system comprises:
a control channel disposed within said elastomeric polymer substrate; and
one or more valves operatively connected to said microfluidic channel to regulate fluid flow through said microfluidic channel, wherein each of said valves comprises a portion of said elastomeric polymer substrate that is located between said control channel and said microfluidic channel, and wherein each of said valves is capable of being deflected into or retractable from said microfluidic channel upon which said valve operates in response to an actuation force applied to said control channel, said valve when positioned in said microfluidic channel is capable of affecting fluid flow therethrough. Tthe means for introducing the fluid into the microfluidic device can comprise a fluid pump comprising at least one of such valve system.

Yet in another embodiment, the microfluidic channel further comprises a narrow section, wherein a significantly higher force is required to introduce the fluid into the narrow section compared to the other section of the microfluidic channel. Thus, the method can include introducing the fluid into the microfluidic channel with the amount of force that is less than the amount of force required to introduce the fluid into the narrow section of the microfluidic channel. In this manner, a predetermined amount of the fluid is introduced into the microfluidic channel.

Still in another embodiment, the fluid inlet comprises a capillary element attached to said body structure, and wherein the capillary element comprises a capillary channel disposed therethrough and in fluid communication with the microfluidic channel. Alternatively, the fluid inlet comprises an elongated capillary protuberance disposed within the body structure, and wherein the elongated capillary protuberance comprises a capillary channel which is in fluid communication with the microfluidic channel.

Still yet in another embodiment, the means for introducing the fluid into the microfluidic device comprises using an external device which is operatively connected to a microfluidic channel. In one particular embodiment, the external device is a vacuum device which is operatively connected to an orifice disposed within the body structure, wherein the orifice is in fluid communication with the microfluidic channel. In another specific embodiment, the means for transporting the fluid comprises a pressurizing device operatively connected to the microfluidic channel. In this manner, when the port is in contact with the fluid and the fluid container is sealed and pressurized by the pressurizing device, the fluid flows from the fluid container into the microfluidic channel.

Yet another aspect of the present invention provides a method for dispensing a fluid from a microfluidic device comprising:
a body structure comprising an elastomeric polymer substrate;
a microfluidic channel disposed within the elastomeric polymer substrate and comprising the fluid therein;
a fluid outlet in fluid communication with the microfluidic channel for dispensing the fluid from the microfluidic channel; and
a pump disposed within the elastomeric polymer substrate and operatively connected to the microfluidic channel such that fluid flow through the microfluidic channel can be regulated by the pump,
said method comprising dispensing the fluid from the microfluidic channel using the pump.

In one embodiment, the microfluidic device farther comprises at least one valve system, wherein each valve system comprises:
a control channel disposed within the elastomeric polymer substrate; and
one or more valves operatively connected to the microfluidic channel to regulate fluid flow through the microfluidic channel, wherein each of the valves comprises a portion of the elastomeric polymer substrate that is located between said control channel and the microfluidic channel, and wherein each of the valves is capable of being deflected into or retractable from the microfluidic channel upon which the valve operates in response to an actuation force applied to the control channel, the valve when positioned in the microfluidic channel is capable of affecting fluid flow therethrough. In one particular embodiment, the pump comprises one or more such valve systems.

In another embodiment, the fluid is dispensed through the fluid outlet that is disposed within an interstitial surface defined by a passageway that extends from a first surface to a second surface of the body structure. The fluid dispensed into the passageway can be held within the passageway due primarily to capillary action and/or surface tension. In such instances, a solvent can be introduced into the passageway to remove the fluid from the passageway.

The fluid can be dispensed from the microfluidic channel into a sample holder. In one specific embodiment, the microfluidic device comprises a plurality of fluid outlets and the sample holder comprises a plurality of sample holding chambers. In this manner, a large number of same or different fluid samples can be placed into a sample holder at one time.

In one embodiment, the fluid outlet comprises an elongated capillary protuberance disposed within the body structure, and wherein the elongated capillary protuberance comprises a capillary channel which is in fluid communication with the microfluidic channel. Alternatively, the fluid outlet comprises a capillary element attached to the body structure, and wherein the capillary element comprises a capillary channel disposed therethrough and in fluid communication with the microfluidic channel.

Yet in another embodiment, each actuation of the pump dispenses a predetermined amount of the fluid sample.

Still in another embodiment, the pump comprises a plurality of valve systems.

Still yet in another embodiment, the microfluidic channel is an integrated microfluidic channel comprising at least first and second intersecting microscale fluidic channels, wherein the first microscale fluidic channel is in fluid communication with the fluid outlet. In addition, the microfluidic device can further comprise a pair of valve systems operatively disposed with respect to one another such that when the each valve of the pair of valve system extends into the microfluidic channel a holding space is formed between the valves in which the fluid can be retained. This allows placement of a predetermined amount of fluid within the holding space and removing the excess fluid from the microfluidic channel prior to dispensing the fluid.

Still another aspect of the present invention provides, a method for producing a microfluidic fluid sampling device, said method comprising:

producing a first elastomeric layer comprising a top surface, a bottom surface and an orifice;

producing a second elastomeric layer comprising a top surface, a bottom surface and a microscale recess disposed on the bottom surface;

attaching the bottom surface of the first elastomeric layer on to the top surface of the second elastomeric layer;

creating an orifice on the second elastomeric layer such that the orifice on the first elastomeric layer becomes operatively connected to and in fluid communication with the microscale recess located on the bottom surface of the second elastomeric layer; and attaching a base layer to the bottom surface of the second elastomeric layer, thereby forming a microfluidic channel from the microscale recess, wherein the microfluidic channel is disposed within the interface of the second elastomeric layer and the base layer.

In one embodiment, the base layer comprises an orifice such that when the base layer is attached to the bottom surface of the second elastomeric layer the orifice on the base layer is in fluid communication with the microfluidic channel that is formed on the interface of the second elastomeric layer and the base layer. The method can further comprise attaching a capillary element, which comprises a capillary channel disposed therethrough, to the microfluidic device by inserting the capillary element into the orifice on the first elastomeric layer or the bottom layer such that the capillary channel is in fluid communication with the microfluidic channel.

In another embodiment, the first elastomeric layer comprises a second orifice, and said method further comprising creating a second orifice on the second elastomeric layer prior to attaching the base layer to the second elastomeric layer, such that the second orifice on the first elastomeric layer becomes operatively connected to and in fluid communication with the microscale recess located on the bottom surface of the second elastomeric layer. The method can further comprise attaching a capillary element, which comprises a capillary channel disposed therethrough, to the microfluidic device by inserting the capillary element into one of the orifices on the first elastomeric layer such that the capillary channel is in fluid communication with the microfluidic channel.

Still in another embodiment, the first elastomeric layer further comprises a microscale recess on the bottom surface such that when the bottom surface of the first elastomeric layer is attached to the top surface of the second elastomeric layer, the microscale recess on the bottom surface of the first elastomeric layer forms a control channel disposed within the interface of the first elastomeric layer and the second elastomeric layer.

BRIEF DESCRIPTION OF THE DRAWINGS

FIGS. 5A–5C illustrate a variety of methods for fabricating a microfluidic device of the present invention with an integrated capillary element;

FIG. 11A shows a tapered port to reduce a droplet formation on the surface of microfluidic device;

FIGS. 11B and 11C are illustrations of a tapered microfluidic channel near the port for dispensing the fluid in a jet-spray fashion;

FIGS. 12A–12D illustrate microfluidic channel and control channel configurations and their use for dispensing a fixed amount of fluid;

DEFINITIONS

Figure 1A:
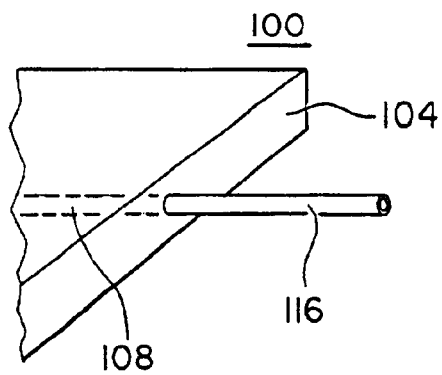
FIG. 1A shows one embodiment of a microfluidic device of the present invention comprising a capillary element.

"Microfluidic device" generally refers a device having channel(s) which are generally fabricated at the micron or submicron scale, e.g., having at least one cross-sectional dimension of about 1000 $\mu$m or less, preferably about 500 $\mu$m or less, and more preferably about 250 $\mu$m or less.

"Microfabricated" refers to the size of features of an elastomeric structure fabricated in accordance with an embodiment of the present invention. In general, variation in at least one dimension of microfabricated structures is controlled to the micron level, with at least one dimension being microscopic, i.e., about 1000 $\mu$m or less.

"Microfluidic channel" refers to a channel (i.e., a conduit) within the microfluidic device which is primarily used to carry a fluid.

"Control channel" refers to a recess or channel within the microfluidic device which is used primarily to control the flow of fluid within the microfluidic channel.

The term "overlaying" refers to a relative position a control channel and a microfluidic channel, such that at least a portion of the control channel is separated from at least a portion of the microfluidic channel by a thin membrane.

"Membrane" refers to the deflectable portion separating a control channel (or control recess) and a microfluidic channel. Actuation of the membrane (also referred to as "actuation of the control channel", especially in the case of pneumatic actuation) causes the thin membrane to deflect into the microfluidic channel.

"Capillary element" refers to an element having a capillary channel therethrough, wherein the cross-sectional dimension of the capillary channel is in the order of micron or submicron scale. Exemplary capillary elements include capillary tubes which are made of quartz, silicate, metal, plastic and other materials known to one skilled in the art.

"Fluid" refers to a gas or, preferably, a liquid medium which can comprise a soluble analyte or a sample.

DETAILED DESCRIPTION OF THE PRESENT INVENTION

The amount of sample required for analysis or synthesis using a microfluidic device is typically on the order of nanoliters and even picoliters. Current structures and methods for transporting a fluid to and from microfluidic devices generally result in the transfer of a much greater volume of fluid than is needed. For example, microfluidic devices typically require nanoliters or picoliters of fluid; however, currently there is no efficient interface available between conventional fluid dispensing equipment and a microfluidic device which allow transfer of such a small amount of fluid. Many conventional fluid dispensing devices typically can not dispense a fluid in amounts less than about 0.1 $\mu$L. Thus, current methods of introducing a fluid to microfluidic devices require $\geq 1$ $\mu$L of fluid, which negates one of the primary advantages of using microfluidic devices.

In addition, other microfluidic devices require electroosmotic force to transport a fluid to and from a microfluidic channel. Since the electroosmotic force requires an electric field, suitable fluids must contain ions. Therefore, the scope of utility of these microfluidic devices are limited. For instance, organic solvents (which are not conductive) cannot be used.

The present invention provides microfluidic devices and systems for transferring or transporting a fluid to and from a microfluidic channel located within the polymer substrate and methods for using the same.

The present invention will now be described with regard to the accompanying drawings which assist in illustrating various features of the invention. However, it should be appreciated that the drawings do not constitute limitations on the scope of the present invention. Throughout the drawings, like numbered items represent same elements of the invention. For the sake of brevity and clarity, most figures show only one microfluidic channel and one control channel (if any); however, it should be appreciated that typical microfluidic devices comprise a plurality of microfluidic channels and control channels. In addition, while the present invention is described in reference to introduction (or injection) of a fluid into the microfluidic channel, unless otherwise specifically stated, microfluidic devices and systems can also be used to dispense (or eject) a fluid from the microfluidic channel.

I. General Organization of a Microfluidic Device

Figure 1B:
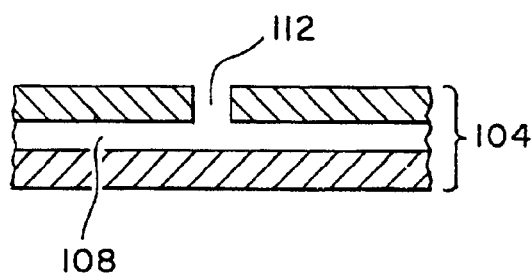
FIG. 1B is a cross-sectional view of a microfluidic device comprising a port in fluid communication with a microfluidic channel.
Figure 1C:
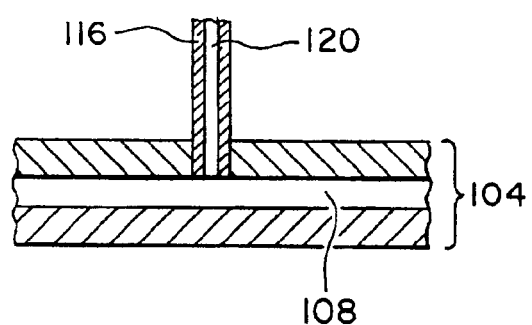
FIG. 1C is a cross-sectional view of a microfluidic device comprising a capillary element within a port.

FIGS. 1A–1C disclose representative diagrams of exemplary microfluidic devices 100 according to the present invention. As shown, microfluidic devices of the present invention include a body structure comprising an elastomeric polymer substrate 104. The microfluidic device shown in FIGS. 1A–1C also include microfluidic channel 108 disposed within the elastomeric polymer substrate 104 and a port 112 in fluid communication with the microfluidic channel 108. In addition, the microfluidic device 100 also comprises a means for transporting the fluid (not shown) to and from the microfluidic channel 108.

Microfluidic devices of the present invention can further comprise a capillary element 116 which is inserted into the port 112. The capillary element 116 comprises a capillary channel 120 which is in fluid communication with the microfluidic channel 108. The capillary element 116 can be permanently or removably attached to the elastomeric polymer substrate 104. When the capillary element 116 is removably attached, one can easily interchange the capillary element 116 to suit a particular need. Unlike conventional microfluidic devices which are typically made of a stiff or relatively non-elastic material, microfluidic devices of the present invention are comprised of an elastomeric polymer substrate. The elastomeric polymer substrate 104 allows easy integration of the capillary element 116 with the port 112. Moreover, when the capillary element 116 is inserted into the port 112, the elastomeric polymer substrate 104 forms a hermetic seal with the capillary element 116. Alternatively, the capillary element 116 can be permanently attached to the microfluidic device as discussed in detail below.

Figure 2A:
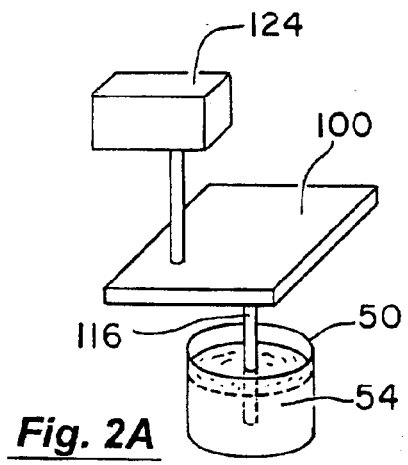
FIG. 2A is a schematic illustration of introducing a fluid into the microfluidic device using a vacuum device.
Figure 2B:
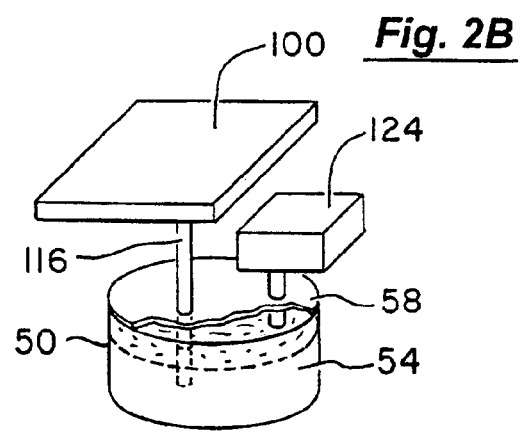
FIG. 2B is a schematic illustration of introducing a fluid into the microfluidic device using a pressurizing device.

Construction of the microfluidic device with an elastomeric polymer allows a variety of fluid transporting means to be utilized with microfluidic devices of the present invention, including conventional microfluidic fluid transporting means, such as using an electroosmotic force. However, as stated above, use of electroosmotic force requires an ionic solution, and therefore its utility is rather limited. Other methods for transporting a fluid to and from the microfluidic channel include using an external device 124, as shown in FIGS. 2A and 2B. The external device can be a vacuum, a pressurizing device or other devices which can transport the fluid to and/or from the microfluidic device 100.

Figure 3A:
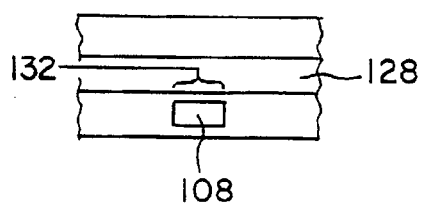
FIG. 3A is a cross-sectional view of a microfluidic device comprising a microfluidic channel and a control channel which is separated by a thin elastomeric polymer membrane.
Figure 3B:
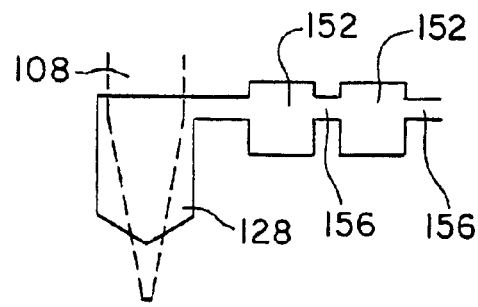
FIG. 3B is a schematic illustration of a control channel comprising a tapered tip and capacitors.
Figure 3C:
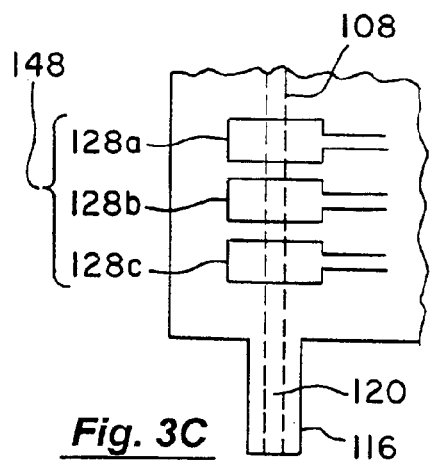
FIG. 3C is a schematic illustration of a microfluidic device of the present invention having a peristaltic pump comprising a plurality of control channels.

A particularly preferred fluid transporting means comprises one or more control channels 128 disposed within the elastomeric polymer structure 104 and overlaying the microfluidic channel 108, as schematically illustrated in FIGS. 3A–3C. Because the microfluidic devices of the present invention comprise an elastomeric polymer, the control channels 128 can be actuated by a variety of means, such as pneumatic, magnetic, and electrostatic as described in detail below. Actuating the control channel 128 deflects a thin elastic membrane 132 that is present between the microfluidic channel 108 and the control channel 128. By designing the control channel 128 such that the thin elastic membrane 132 is deflected down into the microfluidic channel 108 from one direction to another, the fluid may be pushed in a directional manner within the microfluidic channel 108. See, for example, FIG. 3B. Alternatively, a plurality of control channels 128 can be actuated in a particular sequence to create a peristaltic pump action to move the fluid within the microfluidic channel 108. See, for example, FIG. 3C. The control channels 128 and microfluidic channel 108 can be designed such that actuation of the control channels 128 allow more precise control over the amount of fluid sampling relative to conventional microfluidic devices.

II. Suitable Elastomeric Materials

Suitable elastomeric polymer substrate materials are generally selected based upon their compatibility with the conditions present in the particular operation to be performed by the device. Such conditions can include extremes of pH, pressure within microfluidic channels and/or control channels, temperature, and ionic concentration, etc. Additionally, elastomeric polymer substrate materials are also selected for their inertness to critical components of an analysis or synthesis to be carried out by the device. Alternatively, elastomeric polymer substrate materials can be coated with suitable materials, as discussed in detail below.

Microfluidic devices which include an optical or visual detection element, are generally fabricated, at least in part, from transparent materials to allow, or at least, facilitate that detection. Alternatively, transparent windows of, e.g., glass or quartz, may be incorporated into the device for these types of detection elements. Additionally, the elastomeric polymer can have linear or branched backbones, and can be crosslinked or non-crosslinked.

The elastic members (i.e., layers) of the devices of the present invention comprising two or more elastic layers can be fabricated from a wide variety of elastomers. In an exemplary aspect, elastomeric layers can be fabricated from polyurethanes, isoprene polymers, and preferably silicone rubber. However, other suitable elastomers can also be used. It should be appreciated that the present invention is not limited to these types or even families of polymers; rather, nearly any elastomeric polymer is suitable. An important requirement for the preferred method of fabrication of the present elastomers is the ability to bond multiple layers of elastomers together. In the case of multilayer soft lithography, layers of elastomer are cured separately and then bonded together. This scheme requires that cured layers possess sufficient reactivity to bond together. Either the layers can be of the same type, and are capable of bonding to themselves (A to A), or they can be of two different types, and are capable of bonding to each other (A to B). Another possibility is to use an adhesive between layers.

The elasticity exhibited by the elastomeric polymer substrate can be characterized by a Young's modulus. In general, elastomeric polymer substrates should have a Young's modulus of from about 1 Pa to about 1 Tpa. Preferably, elastomeric polymer substrates of the present invention have a Young's modulus of from about 10 Pa to about 100 GPa, preferably from about 20 Pa to 1 GPa, more preferably from about 50 Pa to about 10 MPa, and more preferably from about 100 Pa to about 5 MPa.

Given the tremendous diversity of polymer chemistries, precursors, synthetic methods, reaction conditions, and potential additives, there are a huge number of possible elastomer systems that could be used to make chemical reaction apparatus of the present invention. Variations in the materials used will most likely be driven by the need for particular material properties, i.e., solvent resistance, stiffness, gas permeability, temperature and/or pH stability, and/or reasonable adhesion to the solid support, if used.

There are many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene:

Polyisoprene, polybutadiene, and polychloroprene are all polymerized from diene monomers, and therefore on the average have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded.

Polyisobutylene

Pure polyisobutylene has no double bonds, but is crosslinked to use as an elastomer by including a small amount (~1%) of isoprene in the polymerization. The isoprene monomers give pendant double bonds on the polyisobutylene backbone, which can then be vulcanized as above.

Poly(styrene-butadiene-styrene)

Poly(styrene-butadiene-styrene), i.e., SBS, is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes

Polyurethanes are produced from di-isocyanates (A—A) and di-alcohols or di-amines (B—B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A—A in one layer and excess B—B in the other layer.

Silicones

Silicone polymers probably have the greatest structural variety, and almost certainly have the greatest number of commercially available formulations. The vinyl-to-(Si—H) crosslinking of RTV 615 (which allows both heterogeneous multilayer soft lithography) is only one of several crosslinking methods used in silicone polymer chemistry.

Cross Linking Agents

In addition to the use of the simple "pure" polymers discussed above, crosslinking agents can be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

Other Materials

In addition, silicon containing materials such as chlorosilanes can also be used. Suitable silicon containing materials include, but are not limited to, methyl-, ethyl-, and phenylsilanes, for example, polydimethylsiloxane (PDMS) such as Dow Chemical Corp. Sylgard 182, 184 or 186; and alipathic urethane diacrylates such as Ebecryl 270 or Irr 245 which are available from UCB Chemical.

The following is a non-exclusive list of elastomeric materials which can be utilized in connection with the present invention: epoxy acrylates such as Ebecryl resins 3500® and 3708®, polyisoprene, polybutadiene, polychloroprene, polyisobutylene, poly(styrene-butadiene-styrene), polyurethanes, silicone polymers, poly(bis (fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

Doping and Dilution

Elastomers can also be "doped" with uncrosslinkable polymer chains of the same class. For instance GE RTV 615 can be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "inert" polymer chains, so this is called "dilution". RTV 615 cures at up to 90% dilution, with a dramatic reduction in Young's modulus.

Other examples of doping of elastomer material can include the introduction of electrically conducting or magnetic species, as described in detail below in conjunction with alternative methods of actuating the membrane of the device. Should it be desired, doping with fine particles of material having an index of refraction different than the elastomeric material (i.e., silica, diamond or sapphire) is also contemplated as a system for altering the refractive index of the material. Strongly absorbing or opaque particles can be added to render the elastomer colored or opaque to incident radiation. This can conceivably be beneficial in sampling a fluid which may be photolabile.

Finally, by doping the elastomer with specific chemical species, these doped chemical species can be presented at the elastomer surface, thus serving as anchors or starting points for further chemical derivatization or providing chemical resistance.

III. Pre-Treatment and Surface Coating

Once the elastomeric material has been molded or etched into the appropriate shape, it may be necessary to pre-treat the material in order to facilitate operation in connection with a particular application. For example, in order to reduce or prevent elastomer from dissolving in the solvent or to prevent a chemical reaction with the fluid sample, one can coat the inner walls of the microfluidic channels 104 with polypropylene, polyvinylidene fluoride, Viton® or other suitable inert materials.

While control of the flow of the fluid through the device is generally described throughout the application as utilizing applied air pressure in the control channels, other fluids can be used. For example, air is compressible, and thus experiences some finite delay between the time of application of pressure by the external activator (e.g., solenoid valve) and the time that this pressure is experienced by the membrane. In an alternative embodiment of the present invention, pressure could be applied from an external source to a noncompressible fluid such as water or hydraulic oils, resulting in a near-instantaneous transfer of this pressure to the membrane. However, if the displaced volume of the valve is large or the pressure channel is narrow, higher viscosity of a control fluid may contribute to delay in actuation. The optimal medium for transferring pressure will therefore depend upon the particular application and device configuration, and both gaseous and liquid media are contemplated by the invention.

IV. General Fabrication Methods for a Microfluidic Device

Microfabrication of microfluidic channels and other microscale elements into the surface of the substrate 104 can be carried out using any number of microfabrication techniques that are well known in the art. Microfabrication typically involves semiconductor or MEMS fabrication techniques such as photolithography and spincoating that are designed to produce feature dimensions on the microscopic level, which typically requires a microscope to reasonably resolve/image the structure. Some aspects of the microfluidic devices of the present invention can be constructed using Multilayer Soft Lithography, a multilayer molding process first described in Unger et al. *Science*, 2000, 288, 113–116, which is incorporated herein by reference in its entirety. Most aspects of the microfluidic devices of the present invention can be constructed using processes disclosed in U.S. patent application Ser. No. 09/605,520, filed Jun. 27, 2000, which is incorporated herein by reference in its entirety. It is to be understood, however, that other suitable methods of fabricating the present microfluidic devices, including modifying the methods disclosed in above incorporated references, are also contemplated. Such microfabrication techniques generally involve polymerizing the elastomeric substrate within a microfabricated mold. Other microfabrication techniques include injection molding techniques or stamp molding methods where large numbers of elastomeric polymer substrates can be produced using, e.g., rolling stamps to produce large sheets of microscale substrates. Subtractive fabrication techniques, where the elastomer is patterned by (e.g.) wet chemical etching, laser cutting, plasma etching, reactive ion etching, mechanical punching, conventional mechanical machining, electronic discharge machining, and the like, are also contemplated in the invention.

When the elastomeric polymer substrate is produced using a mold, the microfluidic device includes an additional base layer which overlays the channeled substrate 104 to enclose and fluidly seal the various microfluidic channels (i.e., to form conduits). The base layer can be attached to the elastomeric substrate by a variety of means, including, but not limited to, thermal bonding, adhesives or a natural adhesion between the two components, as described above. For brevity, the combination of a base layer and the elastomeric polymer substrate which forms microfluidic channel is simply referred herein as the elastomeric polymer substrate.

Figure 4:
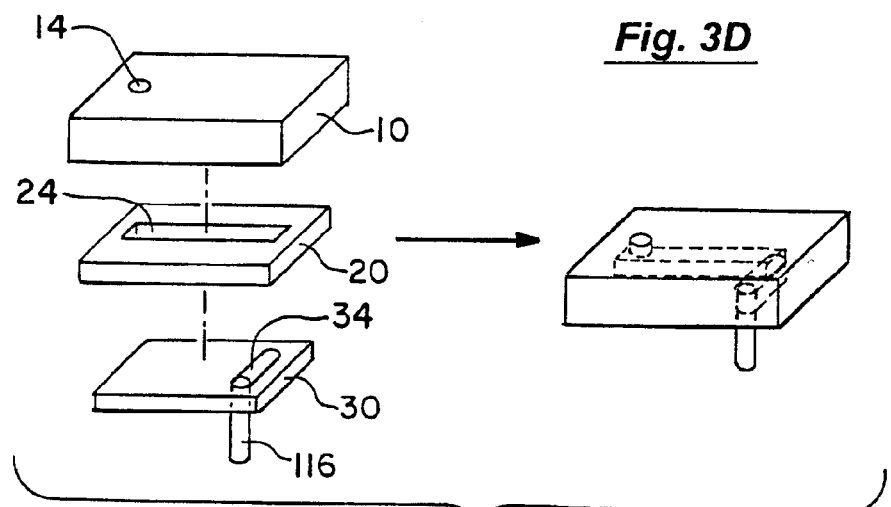
FIG. 4 is a schematic illustration of a method for making a microfluidic device comprising three layers.

One particular embodiment for producing the microfluidic device of the present invention is illustrated in FIG. 4. In this particular method, a first elastomeric polymer layer 10 comprising a first layer containing control channels vias to the control lines 14 and a second elastomeric polymer layer 20 comprising a fluidic channel 24 are produced using any of the methods discussed above, e.g., softlithography or polymerizing the elastomeric substrate within a microfabricated mold. The first layer 10 and the second layer 20 are then attached such that the control channels 14 are aligned with the fluidic channel 24. By attaching a base layer 30, which can be an elastomeric polymer or a non-elastic solid, such as glass, silicon, quart, plastic, etc., to the second layer 20 on the side opposite the first layer 10, microfluidic channel 108 is formed from 24. The base layer can comprise a fluidic channel 34 which when attached to the second layer 20 also forms the port 112. These layers are preferably elastomeric polymers. In this manner, a capillary element 116 and/or an external device 124 (not shown in FIG. 4) for injecting or dispensing the fluid can be easily attached to the microfluidic device 100. See FIG. 2A. Alternatively, the first elastomeric layer 10 can comprise at least two ports, thereby producing microfluidic device similar to the one shown in FIG. 2A but with the external device 124 and the capillary element 116 attached on the same side of the microfluidic device.

In addition, a fourth layer (not shown) comprising a channel can be attached to the first layer such that the channels on the fourth layer forms a control channel overlaying the microfluidic channel. The control channels would actually be in layer 10

Preferably, these polymeric layers are comprised of a same material, thereby forming a monolithic structure.

One particular embodiment for producing the microfluidic device of the present invention is illustrated in FIG. 4. In this particular method, a first elastomeric polymer layer 10 comprising a first layer containing control channels and fluidic vias 14 and a second elastomeric polymer layer 20 comprising a fluidic channel 24 are produced using any of the methods discussed above, e.g., softlithography or polymerizing the elastomeric substrate within a microfabricated mold. The first layer 10 and the second layer 20 are then attached such that the control channels and vias 14 are aligned with the fluidic channel 24. The layer 14 contains the port 112. By attaching a base layer 30, which can be an elastomeric polymer or a non-elastic solid, such as glass, silicon, quart, plastic, etc., to the second layer 20 on the side opposite the first layer 10, microfluidic channel 108 is formed. The base layer can comprise a fluidic channel 34 which when attached to the second layer 20 also forms the port 112. These layers are preferably elastomeric polymers. In this manner, a capillary element 116 and/or an external device 124 (not shown in FIG. 4) for injecting or dispensing the fluid can be easily attached to the microfluidic device 100. See FIG. 2A. Alternatively, the first elastomeric layer 10 can comprise at least two ports, thereby producing microfluidic device similar to the one shown in FIG. 2A but with the external device 124 and the capillary element 116 attached on the same side of the microfluidic device. There aren't any necessarily cavities in these structures. They actually consist of channels and vias.

In addition, a fourth layer (not shown) comprising a channel can be attached to the first layer such that the channels on the fourth layer forms a control channel overlaying the microfluidic channel. The control channels would actually be in layer 10.

V. Preferred Layer and Channel Dimensions

A particular channel dimensions depend on a variety of factors, including the particular elastomer (i.e., polymer substrate) used, the desired fluid flow rate, the viscosity of the fluid being used, the desired actuation means of the control channels 128, etc. In one embodiment of the present invention, microfluidic channels 108 and control channels 128 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, microfluidic channels 108 and control channels 128 have widths of about 1 to 1000 microns. A non-exclusive list of other ranges of widths of microfluidic channels 108 and control channels 128 in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 $\mu$m, 1 $\mu$m, 2 $\mu$m, 5 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 110 $\mu$m, 120 $\mu$m, 130 $\mu$m, 140 $\mu$m, 150 $\mu$m, 160 $\mu$m, 170 $\mu$m, 180 $\mu$m, 190 $\mu$m, 200 $\mu$m, 210 $\mu$m, 220 $\mu$m, 230 $\mu$m, 240 $\mu$m, and 250 $\mu$m.

In another embodiment, microfluidic channels 108 and control channels 128 have depths of about 1 to 100 microns. A non-exclusive list of other ranges of depths of microfluidic channels 108 and control channels 128 in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary microfluidic channel and control channel depths include 0.01 $\mu$m, 0.02 $\mu$m, 0.05 $\mu$m, 0.1 $\mu$m, 0.2 $\mu$m, 0.5 $\mu$m, 1 $\mu$m, 2 $\mu$m, 3 $\mu$m, 4 $\mu$m, 5 $\mu$m, 7.5 $\mu$m, 10 $\mu$m, 12.5 $\mu$m, 15 $\mu$m, 17.5 $\mu$m, 20 $\mu$m, 22.5 $\mu$m, 25 $\mu$m, 30 $\mu$m, 40 $\mu$m, 50 $\mu$m, 75 $\mu$m, 100 $\mu$m, 150 $\mu$m, 200 $\mu$m, and 250 $\mu$m.

The microfluidic channels 108 and control channels 128 are not limited to these specific dimension ranges and examples given herein. The channels (i.e., microfluidic channels and/or control channels) can vary in width in order to affect the magnitude of force required to deflect the membrane 132 as discussed above. Elastomeric structures which include portions having channels of even greater width than described above are also contemplated by the present invention, and examples of applications of utilizing such wider microfluidic channels include fluid reservoir (not shown) and mixing channel structures (not shown).

Elastomeric layer comprising a control channel 128 can be cast thick for mechanical stability. In an exemplary embodiment, elastomeric layer comprising a control channel 128 is 50 microns to several centimeters thick, and more preferably approximately 4 mm thick. A non-exclusive list of ranges of thickness of the elastomer layer comprising a control channel in accordance with other embodiments of the present invention is between about 0.1 micron to 10 cm, 1 micron to 5 cm, 10 microns to 2 cm, 100 microns to 10 mm.

In one aspect of the present invention, the membrane 132 separating a microfluidic channel 108 and a control channel 128 has a typical thickness from about 0.01 to about 1000 microns. Preferably, the thickness of the membrane 132 is from 0.05 to 500 microns, more preferably 0.2 to 250, still more preferably 1 to 100 microns, yet more preferably 2 to 50 microns, and most preferably 5 to 40 microns. As such, in one embodiment, the thickness of elastomeric layer comprising the control channel 128 is about 100 times the thickness of elastomeric layer comprising a microfluidic channel 108. Exemplary thickness of the membrane 132 include 0.01 $\mu$m, 0.02 $\mu$m, 0.03 $\mu$m, 0.05 $\mu$m, 0.1 $\mu$m, 0.2 $\mu$m, 0.3 $\mu$m, 0.5 $\mu$m, 1 $\mu$m, 2 $\mu$m, 3 $\mu$m, 5 $\mu$m, 7.5 $\mu$m, 10 $\mu$m, 12.5 $\mu$m, 15 $\mu$m, 17.5 $\mu$m, 20 $\mu$m, 22.5 $\mu$m, 25 $\mu$m, 30 $\mu$m, 40 $\mu$m, 50 $\mu$m, 75 $\mu$m, 100 $\mu$m, 150 $\mu$m, 200 $\mu$m, 250 $\mu$m, 300 $\mu$m, 400 $\mu$m, 500 $\mu$m, 750 $\mu$m, and 1000 $\mu$m.

VI. Exemplar Construction Techniques and Materials

Preferably, the layers comprising microfluidic channel 108 and control channel 128 are bonded together chemically, using chemistry that is intrinsic to the polymers comprising the patterned elastomeric layers. Most preferably, the bonding comprises two component "addition cure" bonding.

In a preferred aspect, the elastic member layers are bound together in a heterogenous bonding in which the layers have a different chemistry. Alternatively, a homogenous bonding can be used in which the layers would be of the same chemistry. Thirdly, the elastomer layers can optionally be glued together by an adhesive instead. In a fourth aspect, the elastomeric layers can be thermoset elastomers bonded together by heating.

The surface of the elastic layers can also be modified, for example, by flowing through materials such as Viton®, Teflon-AF®, polypropylene, or polyvinylidene flouride, etc. (e.g., dissolved in a solvent) to deposit such material along the inner surface of the microfluidic channels and/or control channels to afford chemical resistance, where necessary. Alternatively, the surface of elastic layer(s) can be modified by chemical treatment or plasma etching to modify the surface directly or to prepare it to receive a coating such as those described above. A coating material can be poured, sprayed, spin-coated, brushed, evaporated, plasma deposited, or flowed through the channels to coat the inner surface of the channels. Alternatively, parts of the elastic layer(s) can be dipped or soaked in a solution to apply the coating material.

In one aspect of homogeneous bonding, the elastomeric layers are composed of the same elastomer material, with the same chemical entity in one layer reacting with the same chemical entity in the other layer to bond the layers together. Bonding between polymer chains of like elastomer layers can result from activation of a cross-linking agent due to light, heat, or chemical reaction.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together can comprise bonding together two layers of silicone rubber each comprising a two-part components. For bonding, one layer can be made with excess of the first component and the other excess of the other component: each layer is cured separately, and when the two layers are brought into contact and cured at elevated temperature, they bond irreversibly forming an integrated elastomer structure.

Alternatively, other bonding methods can be used including activating the elastomer surface, for example, by plasma exposure, so that the elastomer layers/polymer substrate will bond when placed in contact. One possible approach to bonding together elastomer layers composed of the same material is illustrated by Duffy et al. in "Rapid Prototyping of Microfluidic Systems in Pdy (Polydimethylsiloxane)", *Analytical Chemistry* 1998, 70, 4974–4984, which is incorporated herein by reference in its entirety. This paper discusses that exposing polydimethylsiloxane (PDMS) layers to oxygen plasma causes oxidation of the surface, with irreversible bonding occurring when the two oxidized layers are placed into contact. Another approach to bonding together layers of elastomer is set forth by Chiu et al., "Patterned Deposition of Cells and Proteins onto Surfaces by Using Three-Dimensional Microfluidic Systems", *Proc. Natl. Acad. Sci.*, 2000, 97, 2408–2413, which is incorporated herein by reference in its entirety.

Still another approach is disclosed in Anderson et al., "Fabrication of Topologically Complex Three-Dimensional Microfluidic Systems in PDMS by Rapic Prototyping," *Analytical Chemistry*, 2000, 72(14), 3158–3164, which is incorporated herein by reference in its entirety. This approach allows 2–3 layers of elastic members to be formed all at once such that no bonding between elastic member layer is needed.

Yet another approach to bonding together successive layers of elastomer is to utilize the adhesive properties of uncured elastomer. Specifically, a thin layer of uncured elastomer is applied on top of a first cured elastomeric layer. Next, a second cured elastomeric layer is placed on top of the uncured elastomeric layer. The thin middle layer of uncured elastomer is then cured to produce an integrated elastomer structure. Alternatively, uncured elastomer can be applied to the bottom of a first cured elastomer layer, with the first cured elastomer layer placed on top of a second cured elastomer layer. Curing the middle thin elastomer layer again results in formation of an integrated elastomer structure.

Where encapsulation of sacrificial layers is employed to fabricate the elastomer structure, bonding of successive elastomeric layers can be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

VII. Microfluidic Elements

A number of elements that are commonly utilized in the microfluidic devices disclosed herein are described below. It should be recognized that these elements can be considered modules that can be combined in different ways to yield an essentially unlimited number of configurations. Further, using the following elements or modules one can tailor the microfluidic device to include those elements useful for the particular application(s) to be conducted with the device.

A. General

The microfluidic devices disclosed herein are typically constructed by single and multilayer soft lithography (MLSL) techniques and/or sacrificial-layer encapsulation methods. Both of these methods are described in detail by Unger et al. (2000) Science 288:113–116, in U.S. patent application Ser. No. 09/605,520, filed Jun. 27, 2000, in U.S. patent application Ser. No. 09/724,784, filed Nov. 28, 2000, and in PCT publication WO 01/01025, all of which are incorporated herein in their entirety for all purposes. The microfluidic devices provided herein can include a variety of different components that are described in detail infra. These components can be arranged in a large number of different configurations depending upon the particular application. The following sections describe the general components that are utilized in the devices; these sections are followed with exemplary configurations that can be utilized in various types of assays, such as cellular assays and high throughput screening.

Although the devices can be manufactured exclusively from elastomeric materials, this is not a requirement. Thus, the devices need not be monolithic in nature; hybrid devices fusing elastomers and other materials such as silicon, glass or plastic substrates can be utilized. As described in further detail below, the elastomeric materials can be tailored to the particular application by modifying the internal surfaces of the channels of the microfluidic device.

B. Channels

The channels through which solution is transported in the microfluidic devices are typically formed at least in part, if not entirely, from elastomeric compounds. Separated from the flow channels by an elastomeric membrane are control channels which can be actuated to control or regulate solution flow through the flow channels. As described in greater detail below in the section on valves, actuation of the control channel (e.g., pressurization or pressure reduction within the flow channel) causes the elastomeric membrane separating the flow and control channel to be extended into the flow channel, thus forming a valve that blocks solution flow in the flow channel. Typically, the flow and control channels cross one another at an angle.

The flow and control channels can be manufactured from two primary techniques. One approach is to cast a series of elastomeric layers on a micro-machined mold and then fuse the layers together. The second primary method is to form patterns of photoresist on an elastomeric layer in a desired configuration; in particular, photoresist is deposited wherever a channel is desired. These two different methods of forming the desired configuration of flow and control channels, as well as other details regarding channel dimensions and shape, are described in considerable detail in PCT publication WO 01/01025, U.S. application Ser. No. 09/605, 520, filed Jun. 27, 2000, U.S. application Ser. No. 09/724, 784, filed Nov. 28, 2000, and by Unger et al. (2000) Science 288:113–116, each of which is incorporated herein by reference in its entirety.

Figure 19:
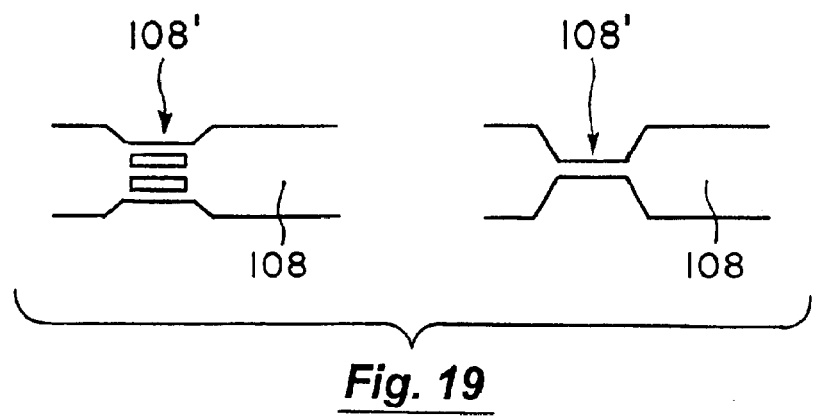
FIG. 19 is a schematic illustration of two examples of microfluidic channels having a narrow section which is capable of preventing further introduction of a fluid into the microfluidic channel when the fluid reaches the narrow section.

A variety of methods are available to allow a precise amount of fluid sampling using the microfluidic device of the present invention. For example, by using a fluid pump which pumps a predetermined amount of the fluid per pumping cycle, one can limit the amount of fluid introduced into the microfluidic channel. An alternative method is illustrated in FIG. 19. In this embodiment, the microfluidic channel 108 comprises a narrow section 108'. As illustrated in FIG. 19, the narrow section 108' can comprise a single channel or a plurality of channels which restricts the flow of fluid. Because the surface tension is generally greater for a smaller cross-sectional areas, in order to introduce the fluid from one part of the microfluidic channel 108 to another part of the microfluidic channel 108 through the narrow section 108', there must be a sufficient force to push or pull the fluid through the narrow section 108'. Thus, by applying a sufficient force to push or pull the fluid through the microfluidic channel 108 but less than the amount of force required to push or pull the fluid through the narrow section 108' one can limit the amount of fluid introduced into the microfluidic channel 108.

C. Sample Inputs

There are a number of different options for introducing a solution into a flow channel. One option is to simply inject solution into a flow channel using a needle, for example. One can also pressurize a container of solution to force solution from the container into a flow channel. A related approach involves reducing pressure at one end of a flow channel to pull solution into a distal opening in the flow channel.

Individual input/inlet lines can be formed that can be loaded manually using single channel micropipettors. The microfluidic devices can be sized according to industry size-specifications (e.g., footprint is 127.76 0.12×85.47 0.12 mm) for plate readers and robotics and are designed to interface with generic multichannel robotic pipettors/samplers with standardized interwell spacings (pitch). Dimensional standards for these types of plate/devices are described at http://www.sbsonline.com, http://www.tomtec.com/Pages/platstan.hmtl). Custom micropipettors that do not conform to this standard can also be utilized. In some systems, an electropipettor that is in fluid communication with a sample input channel is utilized. Micropipettors of this type are described, for example, in U.S. Pat. No. 6,150,180.

Inlets to the microfluidic devices disclosed herein can be holes or apertures that are punched, drilled or molded into the elastomeric matrix. Such apertures are sometimes referred to as "vias." The vias can also be formed using photoresist techniques. For example, metal etch blocking layers used in combination with patterning of photoresist masks and the use of solvents to remove etch blocking layers can be utilized to create vias. Vertical vias between channels in successive elastomer layers can be formed utilizing negative mask techniques. Vias can also be formed by ablation of elastomer material through application of an applied laser beam. All of these techniques are described in greater detail in U.S. application Ser. No. 09/605,520.

Inlets can optionally be lined with couplings (e.g., made of Teflon) to provide a seal with the pipette tips or syringe tip used to inject a solution.

As described further below, pumps formed from elastomeric materials can be used to transport solution through the flow channels. For channels of known dimensions, one can precisely regulate the volume introduced through an inlet from based upon the number of strokes of the pump.

Any sample or solution that is chemically compatible with the elastomeric material from which the microfluidic device is fabricated and which does not contain agents that are too large to pass through the flow channels can be introduced into the device. Examples of suitable samples include, but are not limited to, aqueous buffers or media containing cells, bacteria, viruses, phage, proteins, nucleic acids, small molecules, serum, whole blood or subfractions of blood, organic solvents containing dissolved solutes, oils and mixtures of organic and aqueous solvents.

D. Valves

1. Structure

The valves of the microfluidic devices provided herein are formed of elastomeric material and include a membrane or separating portion that separates a control channel and a flow channel. The valves have two general designs: those that are typically open and those that are normally closed. Valves that are typically open are actuated to block flow through a flow channel by applying pressure to the control channel, thereby deflecting the membrane into the flow channel to restrict flow. In the case of valves that are normally closed, the membrane or separating portion normally extends into the flow channel. However, upon reduction of pressure in the control channel relative to the flow channel, the membrane/separating portion is pulled into the control channel, thus removing the blockage in the flow channel.

Figure 20A:
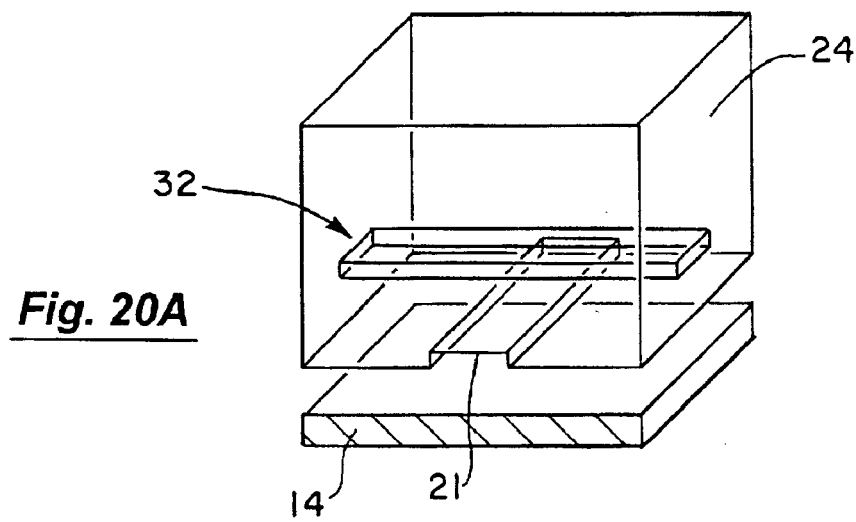
FIGS. 20A and 20B are illustrations of an elastomeric block and the arrangement of a control and flow channel therein.
Figure 20B:
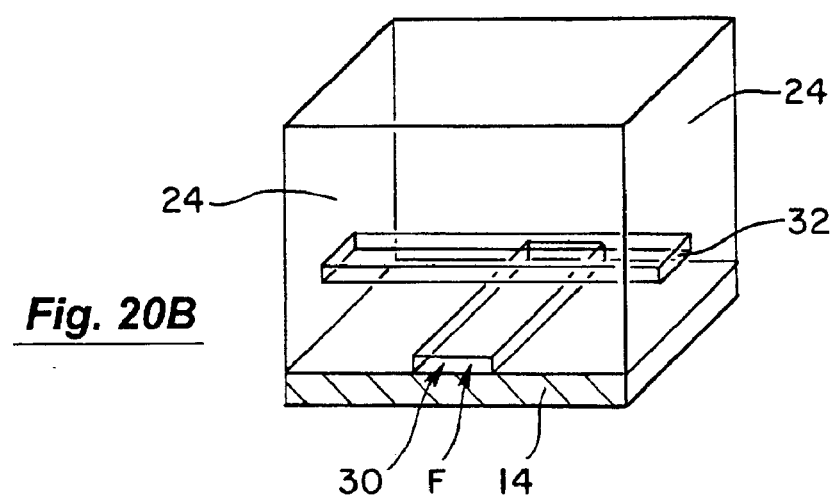
Figure 21A:
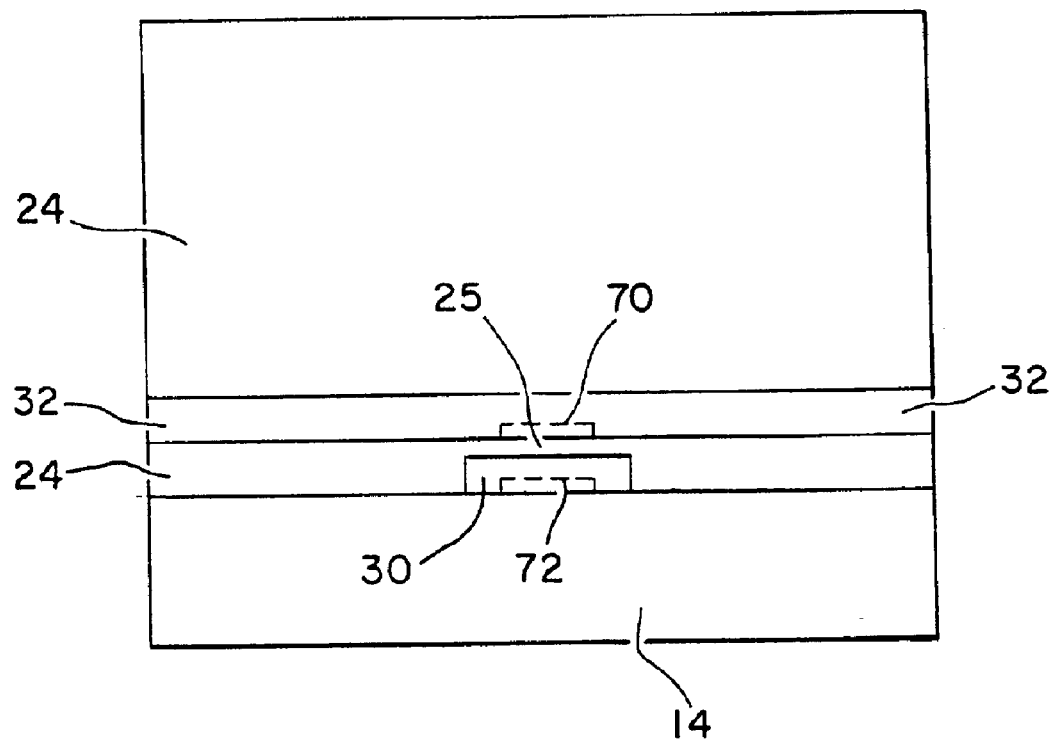
FIG. 21A is a sectional view of an elastomeric block showing the disposition of a flow and control channels with respect to one another in a valve and optional electrodes for actuating the valve.
Figure 21B:
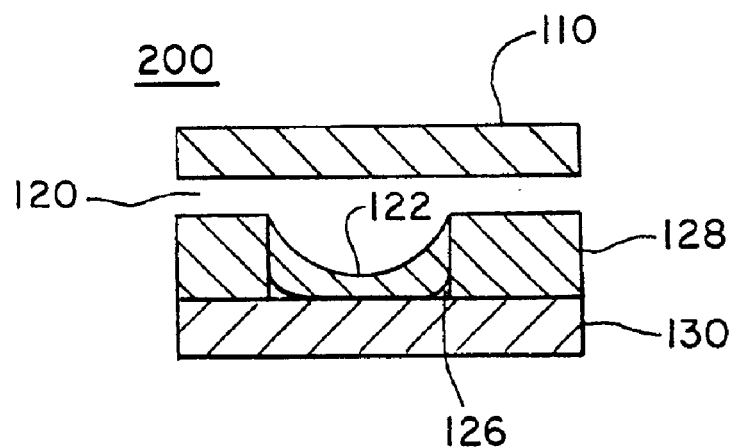
FIG. 21B is a sectional view of an elastomeric block showing blockage of a flow channel when a normally open valve is actuated.

FIGS. 20A and 20B illustrate the general elements of a valve that is typically open. As can be seen, elastomeric structure 24 contains a control channel 32 overlying recess 21 formed from a raised portion of a mold. When the recess in this elastomeric structure is sealed at its bottom surface to planar substrate 14, recess 21 forms a flow channel 30. As can be seen in FIG. 20B and FIG. 21A, flow channel 30 and control channel 32 are preferably disposed at an angle to one another with a small membrane 25 of elastomeric block 24 separating the top of flow channel 30 from the bottom of control channel 32. While these figures show control channels that extend across the device, it should be understood that this need not be the case. The control channel can be a recess sufficiently large such that the membrane is able to provide the desired level of blockage in the flow channel. FIG. 21B illustrates the situation for a normally open elastomeric valve structure 200 in which the valve has been actuated and the flow channel is blocked. In particular, the structure includes a control channel 120 formed within one elastomeric layer 110 that overlays another elastomeric layer 128 which includes a flow channel 126. Elastomeric layer 110 is attached to substrate 130. Because the control channel has been pressurized, the membrane 122 separating the control channel 120 and the flow channel 126 is deflected down into the flow channel 126, thereby effectively blocking solution flow therethrough. Once pressure is released, membrane 122 deflects back up from the flow channel 126 to allow solution flow.

In certain devices, planar substrate 14 is glass. The transparent properties of glass can be useful in that it allows for optical interrogation of elastomer channels and reservoirs. Alternatively, the elastomeric structure can be bonded onto a flat elastomer layer, thereby forming a permanent and high-strength bond. This can prove advantageous when higher back pressures are generated. Hence, the choice of substrate upon which a flow channel is formed (e.g., glass or elastomer) depends in part on the type of detection utilized, as well as the structural requirements of the device.

Figures 22A, 22B:
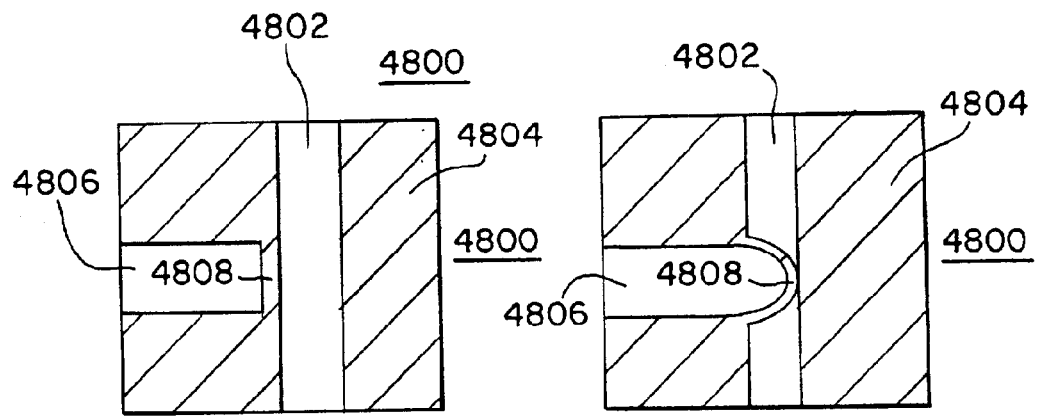
FIGS. 22A and 22B are plan views illustrating the operation of an exemplary side-actuated valve structure.

While the valve shown in FIGS. 20B and 21 involve a system in which a control channel overlays a flow channel, different configurations can be utilized. For example, FIGS. 22A and 22B illustrate a side-actuated valve. More specifically, FIG. 22A shows side-actuated valve structure 4800 in an unactuated position. Flow channel 4802 is formed in elastomeric layer 4804. Control channel 4806 abutting flow channel 4802 is also formed in elastomeric layer 4804. Control channel 4806 is separated from flow channel 4802 by elastomeric membrane portion 4808. A second elastomeric layer (not shown) is bonded over bottom elastomeric layer 4804 to enclose flow channel 4802 and control channel 4806. FIG. 22B shows side-actuated valve structure 4800 in an actuated position. In response to a build up of pressure within control channel 4806, membrane 4808 deforms into flow channel 4802, blocking flow channel 4802. Upon release of pressure within control channel 4806, membrane 4808 relaxes back into control channel 4806 and opens flow channel 4802.

Figure 23A:
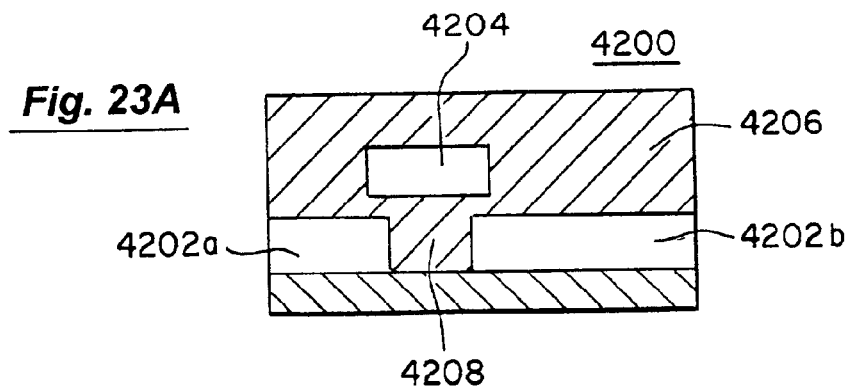
FIGS. 23A and 23B show one example of a normally-closed valve structure.
Figure 23B:
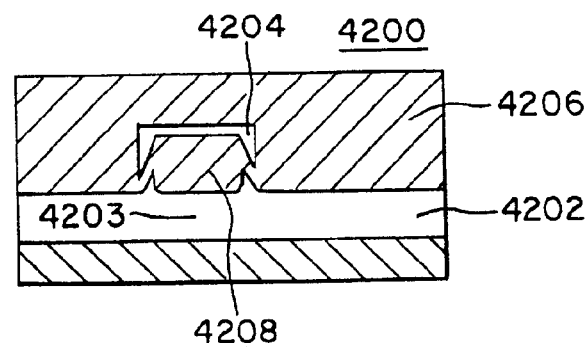

As noted above, the valves can also have a normally closed configuration. FIG. 23A illustrates one example of a normally-closed valve 4200 in an unactuated state. Flow channel 4202 and control channel 4204 are formed in elastomeric block 4206. Flow channel 4202 includes a first portion 4202$a$ and a second portion 4202$b$ separated by separating portion 4208. Control channel 4204 overlies separating portion 4208. As shown in FIG. 23A, in its relaxed, unactuated position, separating portion 4208 remains positioned between flow channel portions 4202$a$ and 4202$b$, interrupting flow channel 4202. FIG. 23B shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force, membrane 4208 projects into control channel 4204, thereby removing the obstacle to solution flow through flow channel 4202 and creating a passageway 4203. Upon elevation of pressure within control channel 4204, separating portion 4208 assumes its natural position, relaxing back into and obstructing flow channel 4202.

It is not necessary that the elastomeric layers that contain the flow and control channels be made of the same type of elastomeric material. For example, the membrane that separates the control and flow channels can be manufactured from an elastomeric material that differs from that in the remainder of the structure. A design of this type can be useful because the thickness and elastic properties of the membrane play a key role in operation of the valve.

2. Options for Actuating Valves

A variety of approaches can be utilized to open or close a valve. If a valve is actuated by increasing pressure in a control channel, in general this can be accomplished by pressurizing the control channel with either a gas (e.g., air) or a fluid (e.g., water or hydraulic oils). However, optional electrostatic and magnetic actuation systems can also be utilized. Electrostatic actuation can be accomplished by forming oppositely charged electrodes (which tend to attract one another when a voltage differential is applied to them) directly into the monolithic elastomeric structure. For example, referring once again to FIG. 21, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e., closing flow channel 30).

Alternatively, magnetic actuation of the flow channels can be achieved by fabricating the membrane separating the flow channels with a magnetically polarizable material such as iron, or a permanently magnetized material such as polarized NdFeB. Where the membrane is fabricated with a magnetically polarizable material, the membrane can be actuated by attraction in response to an applied magnetic field.

Optional electrolytic and electrokinetic actuation systems can also be utilized. For example, actuation pressure on the membrane can be generated from an electrolytic reaction in a recess overlying the membrane. In such an embodiment, electrodes present in the recess are used to apply a voltage across an electrolyte in the recess. This potential difference causes an electrochemical reaction at the electrodes and results in the generation of gas species, thereby giving rise to a pressure differential in the recess. Alternatively, actuation pressure on the membrane can arise from an electrokinetic fluid flow in the control channel. In such an embodiment, electrodes present at opposite ends of the control channel are used to apply a potential difference across an electrolyte present in the control channel. Migration of charged species in the electrolyte to the respective electrodes can give rise to a pressure differential.

Finally, valves can be actuated the device by causing a fluid flow in the control channel based upon the application of thermal energy, either by thermal expansion or by production of gas from liquid. Similarly, chemical reactions generating gaseous products may produce an increase in pressure sufficient for membrane actuation.

3. Options for Selectively Actuating Valves

In order to facilitate fabrication and to reduce the number of control channels in a microfluidic device, often a control channel overlays a number of flow channels. In such instances, pressurization of such a control channel could cause blockage of all the flow channels. Often it is desired to block only selected flow channels, rather than all the flow channels which a control channel abuts. Selective actuation can be achieved in a number of different ways.

Figure 24:
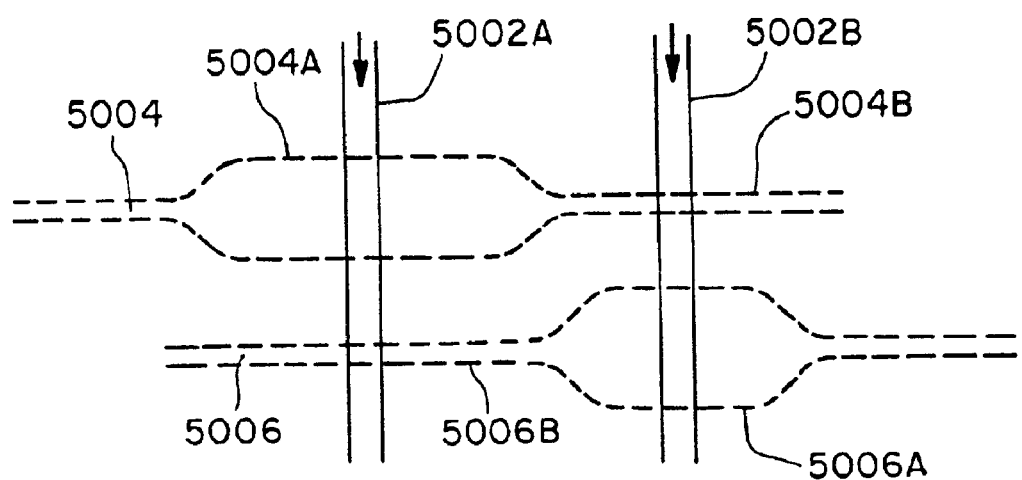
FIG. 24 illustrates one arrangement of control and flow channels that allow for selective blockage of certain flow channels.

One option illustrated in FIG. 24 (see also FIG. 9) is to control the width of the control channels 5004, 5006 at the point at which they extend across the flow channels 5002A and 5002B. In locations where the control channels are wide 5004A, 5006A, pressurization of the control channel 5004, 5006 causes the membrane separating the flow channel and the control channel to depress significantly into the flow channel 5002A, 5002B, thereby blocking the flow passage therethrough. Conversely, in the locations where the control line is narrow 5004B, 5006B, the membrane separating the channels is also narrow. Accordingly, the same degree of pressurization will not result in membrane becoming depressed into the flow channel 5002A, 5002B. Therefore, fluid passage thereunder will not be blocked.

The same general effect can be obtained by varying the width of the flow channel relative to the control channel. Incorporation of an elastomeric support in the section of the flow channel opposite the membrane that is deflected into the flow channel can also prevent complete stoppage of solution flow.

Valves in certain of the figures are represented by single dashed lines if the valve can be utilized to block solution flow through the flow channel. A control channel that crosses a flow channel but which does not act to block the flow channel (for the reasons just described) is represented by a solid arch that arches over a flow channel.

Various other methods of actuating valves are described in the above incorporated U.S. and PCT applications.

E. Pumps

Figure 25A:
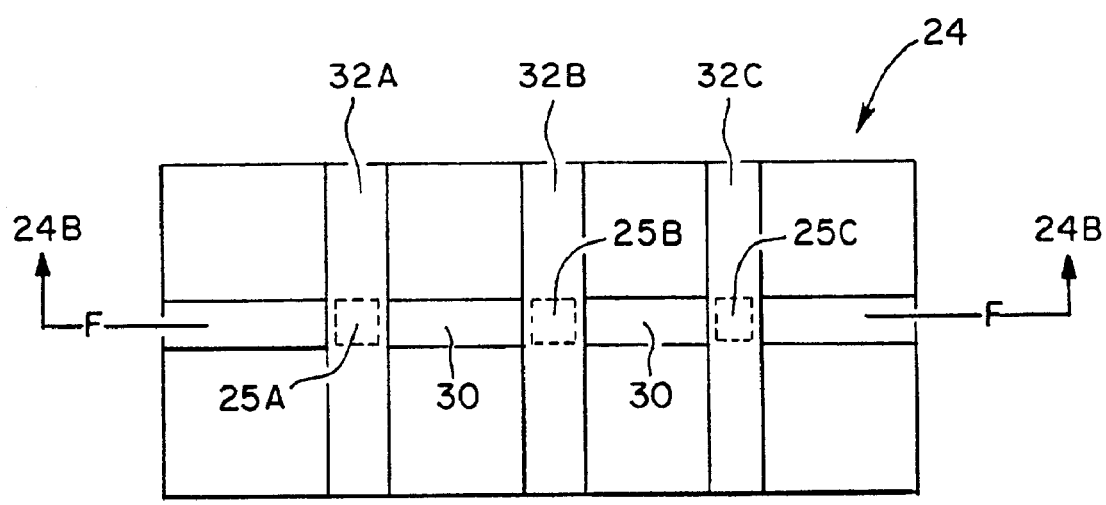
FIG. 25A is a top schematic of the peristaltic pump.
Figure 25B:
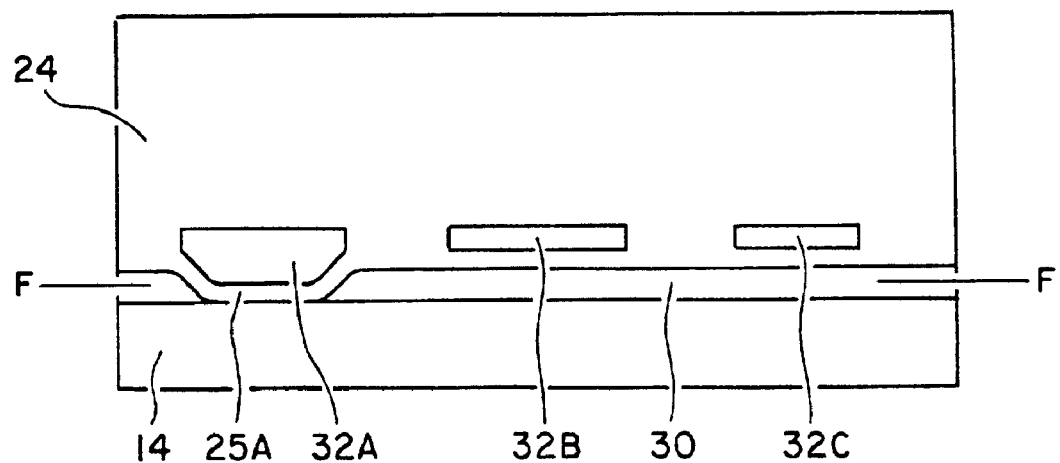
FIG. 25B is a sectional elevation view along line 24B—24B in FIG. 25A.
Figure 26A:
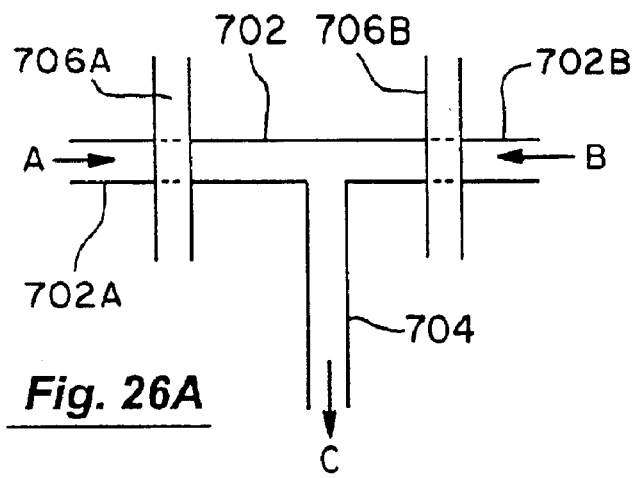
FIGS. 26A–26C are top schematic views of different configurations of flow channels that allow for mixing of solutions.
Figure 26B:
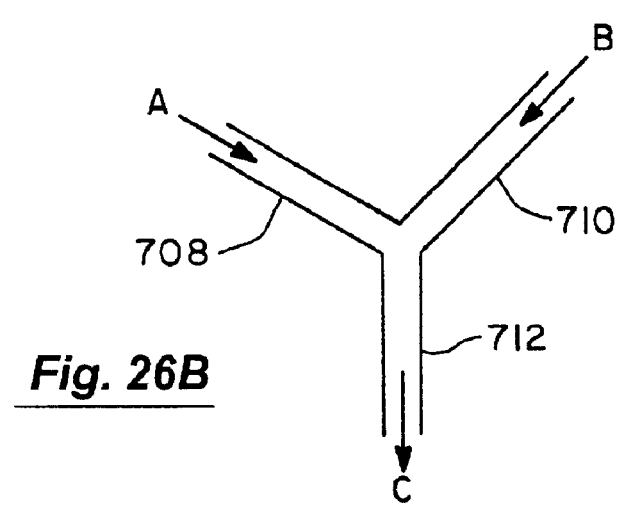
Figure 26C:
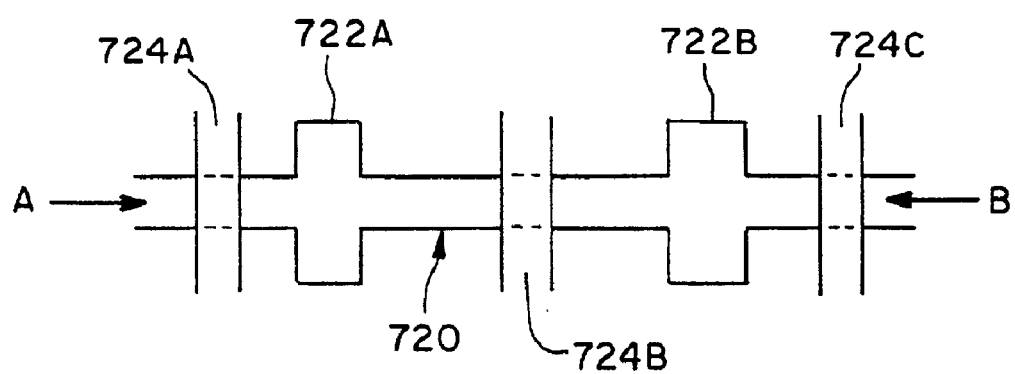

The pumps integrated within the microfluidic devices described herein can be formed from a single control channel or a plurality of control channels that overlay a flow channel. A specific example of a system for peristaltic pumping is shown in FIGS. 25A and 25B. As can be seen, a flow channel 30 has a plurality of generally parallel control channels 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc. Each of control lines 32A, 32B, and 32C is separately addressable. Therefore, peristalsis can be actuated by the pattern of actuating 32A and 32C together, followed by 32A, followed by 32A and 32B together, followed by 32B, followed by 32B and C together, etc. Pumps of this type are denoted in shorthand form in certain of the figures with a series of three parallel dashed lines.

Alternative peristaltic pump embodiments comprising a single control channel 128 are shown in FIGS. 3B and 10A–10E. A single control channel peristaltic pump reduces the complexity of the microfluidic device relative to a similar microfluidic device in which the peristaltic pump comprises a plurality of control channels. The amount of fluid transported in a single control channel peristaltic pump is generally an integer multiple of the fluid volume dispensed by a single actuation of the control channel. Often, a single control channel peristaltic pump is designed to transport a larger quantity of fluid per actuation relative to a multi control channel peristaltic pump. A single control channel peristaltic pump can be more easily controlled to dispense a single, pre-selected volume of fluid. Thus, a single control channel peristaltic pump is generally more efficient than a multi control channel peristaltic pump. However, because the amount of fluid dispensed by a single control channel peristaltic pump is an integer multiple of its fluid amount dispensed in a single actuation, it does not, in general, provide a fluid volume dispense control as fine as a multi control channel peristaltic pump. Moreover, unlike a multi control channel peristaltic pump, a single control channel peristaltic pump can transport a fluid only in one direction which is determined by its design.

Figure 10A:
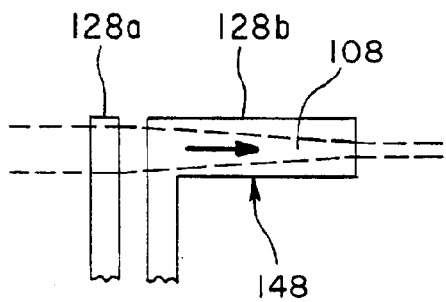
FIG. 10A and 10B are illustrations of a pump comprising a single control channel and a control channel for reducing or eliminating back-flow of the fluid.

In the embodiment illustrated in FIG. 10A, the microfluidic channel 108 underneath the control channel 128b is tapered. When the control channel 128b is actuated (e.g., by pressurization) the thin elastic membrane (not shown) separating the control channel 128b and the microfluidic channel 108 deflects downward beginning from the wide cross-sectional area of the microfluidic channel towards its narrow cross-sectional area. The direction of such actuation and the fluid movement is indicated by the arrow in FIG. 10A. This progressive actuation of the control channel 128b occurs as the actuating force (e.g., pressure) increases because of the ease of deflection of a large thin membrane area relative to the smaller thin membrane area. The amount of fluid potentially flowing backward can be reduced or eliminated by using a second control channel 128a which can serve as an on-off valve. Thus, actuating the control channel 128a and closing the microfluidic channel 108 prior to actuating the control channel 128b minimizes or eliminates the amount of fluid flowing in the direction opposite of the arrow in FIG. 10A.

Figure 10E:
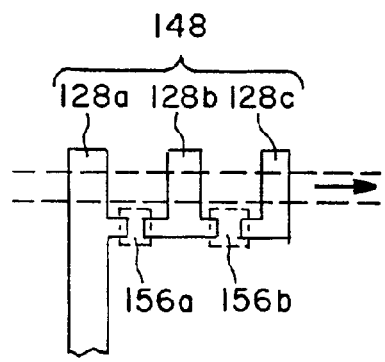
FIG. 10E is an illustration of a single control channel peristaltic pump comprising a normally closed valves.
Figure 10B:
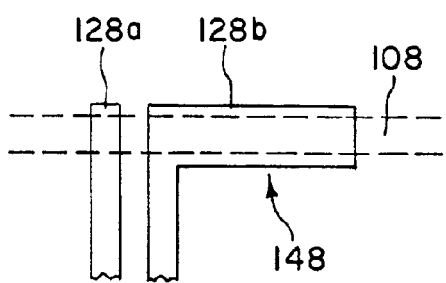

Alternatively, as shown in FIG. 10B, when using a second control channel 128a as an on-off valve, one can use a non-tapered microfluidic channel 108 in combination with a single control channel peristaltic pump configuration. A precise volume of fluid introduced into the microfluidic channel 108 (or dispensed therefrom) can be easily defined by controlling the amount of microfluidic channel volume displaced by the peristaltic pump (i.e., control channel 128b). For example, an approximate volume of the fluid displaced can be calculated by the formula: cross-sectional area (e.g., height×width) of the microfluidic channel 108)× length of control channel 128b overlapping the microfluidic channel 108.

In one particular embodiment of the present invention, a single channel peristaltic pump 148 also comprises one or more capacitor 152 as shown in FIG. 3B. Typically, the capacitor 152 is an area within the control channel line that does not overlap a microfluidic channel but has a larger cross-sectional area than other sections of the control channel. It has been found by the present inventors that the presence of such capacitor(s) provide a smoother actuation of the control channel 128 by providing a delay in control channel actuation. The cross-section area of the capacitor 152 is generally at least about 35 times greater than the cross-section area of the channel 156 leading to the control channel 128, preferably at least about 10 times to about 500 times greater, and more preferably at least about 30 times to about 100 times greater.

In addition, the control channel 128 in FIG. 3B is tapered at the end. This tapering facilitates a substantially complete closing of the control channel 128.

Figure 10C:
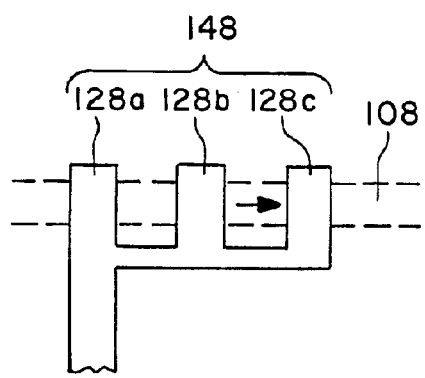
FIGS. 10C and 10D are illustration of a single control channel peristaltic pump.
Figure 10D:
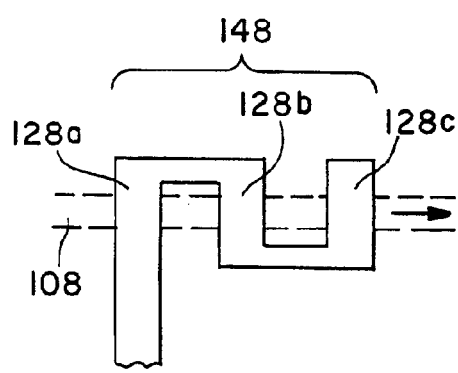

Yet in another embodiment of the present invention, the peristaltic pump 148 can comprise a single control channel which overlaps the microfluidic channel 108 at several locations as shown in FIGS. 10C and 10D. In these configurations, each cross-section area of the control channel (e.g., 128a, 128b and 128c) is greater than each cross-section area that is parallel to the microfluidic channel 108 The pressurization of 128b and c is slower than 128a due to this flow constriction. Thus 128a closes before 128b and c. This sequential actuation "downward" of control channels 128a, 128b, and 128c causes the fluid to move in the direction indicated by the arrows in FIGS. 10C and 10D. It should be noted that there is no need for an on-off control channel within the channel sections that are parallel to the microfluidic channel. The sequential actuation downward of each section of the control channel 128 is due to the difference in the cross-section area. Thus, by varying the cross-section area of each segments of the channel, one can control the order of actuation of each control channel.

As shown in FIG. 10E, in still yet another embodiment of the present invention, the peristaltic pump 148 can comprise a plurality of control channels (e.g., 128a, 128b, and 128c) that are interconnected through a normally closed valve(s) (e.g., 156a and 156b). In this configuration, as the control channel 128a is actuated, e.g., by pressurization, it closes the section of microfluidic channel 108 which is underneath the control channel 128a. As the pressure increases, a normally closed valve 156a is forced open, thereby allowing actuation of control channel 128b and closing the section of microfluidic channel 108 underneath the control channel 128b. This process is repeated until all of the control channels 128a, 128b, and 128c are closed. Unlike the single peristaltic pump configurations shown in FIGS. 3G and 3H, the width of control channel sections above the microfluidic channel need not be larger than the width of control channel sections leading to the normally closed valve 156. Such normally closed valve configuration is disclosed in the above incorporated U.S. patent application Ser. No. 09/605,520.

Variations in the number of control line segments (i.e. 128a, b, c . . . ) can be useful, and are also contemplated by the present invention. The use of two segments rather than three, for instance, reduces the footprint of the device; the use of more segments may increase pumping speed, actuation volume, or resistance to back pressure.

Peristaltic pump 148 comprising a plurality of control channels 128 can be made to sample or dispense a fluid from the microfluidic device 100 depending on the actuation sequence of the control channels 128, e.g., order of actuating control channels 128a–c in FIG. 3C. In contrast, a peristaltic pump 148 having one control channel can be configured to either sample or dispense the fluid at the time of its fabrication. For example, the peristaltic pump 148 in FIGS. 10A–10E can be configured so that the fluid is dispensed out of the microfluidic device or the peristaltic pump 148 can be configured to sample the fluid.

External pumps can also be connected to a flow channel to transport solutions through a channel. Alternatively, a vacuum can be applied to a flow channel to direct fluid flow toward the region of reduced pressure.

F. Capillary Element

Exemplary microfluidic devices comprising a capillary element 116 are illustrated in a variety of figures accompanying this disclosure, including FIGS. 1C, 2B, 3C and 3D. The capillary element 116 can be used as a fluid inlet/outlet system for sampling/dispensing the fluid to and from the microfluidic channel 108. The capillary element 116 can comprise any device which comprises a capillary channel 120 disposed therethrough. Exemplary capillary elements include flexible or non-flexible tubes. Such tubes can be glass, metal, quartz, plastic or other polymers.

Alternatively, the capillary element can be an elongated capillary protuberance of the elastomeric polymer, as exemplified in FIG. 3C. In this particular embodiment, the microfluidic device is microfabricated with a portion of the elastomeric polymeric material comprising the microfluidic channel 108 extending beyond the edge of the microfluidic device. That is the microfluidic device 100 and the capillary element 116 are microfabricated as a single unit. In this embodiment, the elongated capillary protuberance, i.e., protrusion, itself can be considered to be the capillary element 116 with the port 112 being the microfluidic channel opening near, or preferably, at the tip of the elongated capillary protuberance.

When the capillary element 116 and the microfluidic device 100 are fabricated separately, the capillary element 116 can be integrated into the microfluidic device 104 in a variety of ways. For example, the capillary element 116 can fabricated separately and integrated into the microfluidic device 100 during microfabrication process to produce the microfluidic device 100. Alternatively, the capillary element 116 and the microfluidic device 100 can be microfabricated separately and then integrated.

Figure 5C:
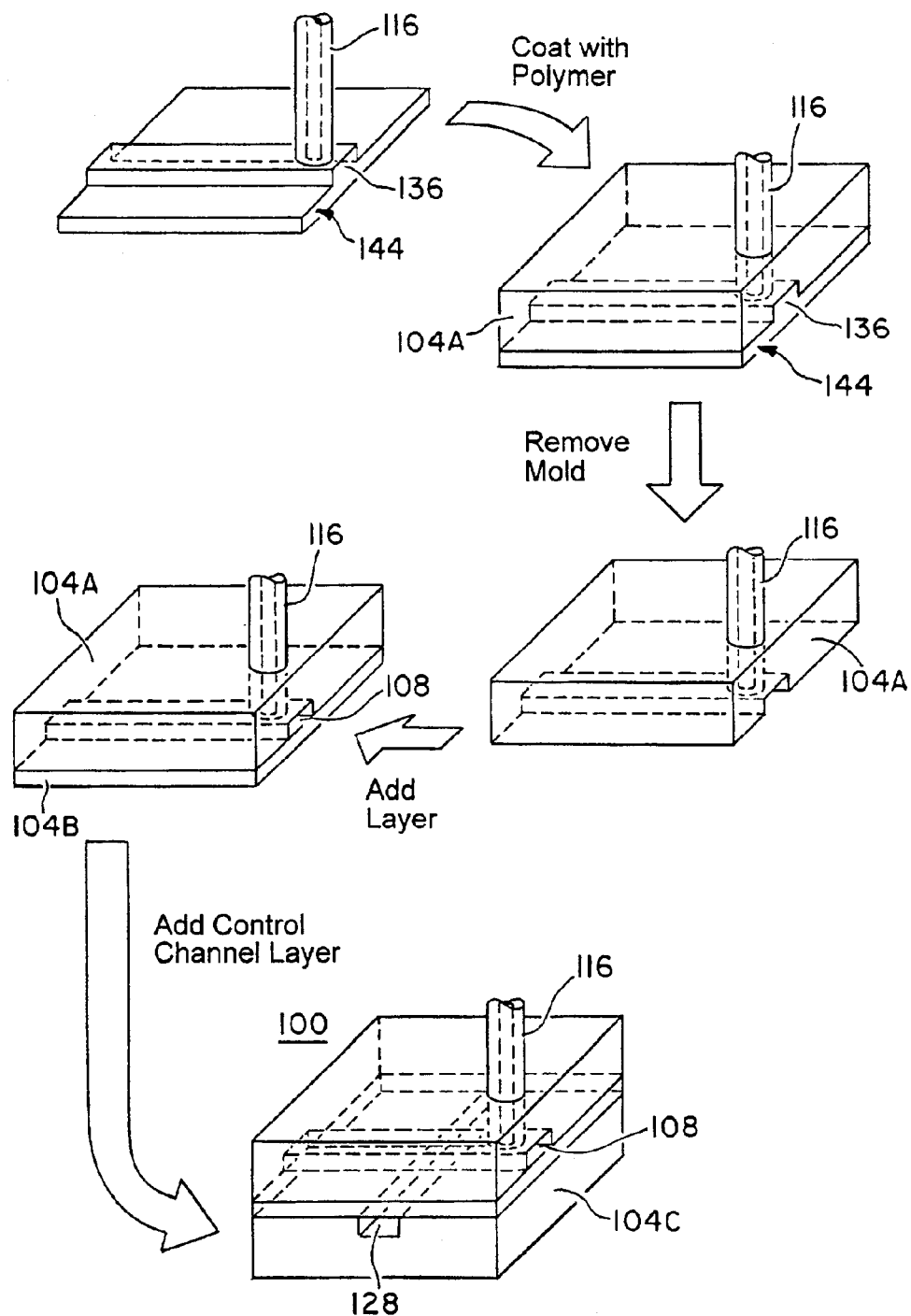

FIGS. 5A–5C illustrates some of the representative methods for integrating the capillary element 116 into the microfluidic device 100 during production of the microfluidic device 100. In one embodiment, as illustrated in FIG. 5A, the capillary element 116 (e.g., capillary tube) is fitted to a protrusion 136 which is attached to a base mold 140. As can be seen, the inner diameter of the capillary element 116 preferably fits over the protrusion 136 such that there is a tight seal between the capillary element 116 and the protrusion 136. The capillary element 116 can be a soft tubing (e.g., silicone rubber) which is flexible. The shape of the protrusion 136 generally determines the shape of the port 112.

Alternatively, as shown in FIGS. 5B and 5C the capillary element 116 is placed directly on the base mold 140. The base mold 140 can comprise a protrusion 136 (FIG. 5B (i)) or it can simply be a flat surface. In order to prevent any elastomeric polymer substrate 104 or its precursor from entering the capillary element 116, the base mold 140 and/or the capillary element 116 can be heated such that the capillary element 116 melts at the interface between the base mold 140 and the capillary element 116 thereby forming a tight seal. The base mold 140 is then coated with the elastomeric polymer precursor (e.g., preferably an elastic polymer such as RTV polymer) material 104A so that the elastomeric polymer precursor material 104A and the capillary element 116 are in an intimate contact with one another. Preferably, the elastomeric polymer precursor material 104A forms a permanent bond with the capillary element 116 (before, during or after curing the polymer precursor material). After the polymer precursor material 104A has been cured, the base mold 140 along with the protrusion 136 (if any) is removed from the cured elastomeric polymer substrate. This layer is then attached to another polymer substrate layer comprising a channel. The combined layer then forms a microfluidic channel 108 which is in a fluid communication with the capillary channel 120. The control channels can be added to the microfluidic device by simply adding another layer (see FIG. 5C). For example, by adding another layer of the polymer substrate 104 with channel(s) on the side opposite the capillary element 116 containing side allows formation of control channel(s).

In FIG. 5C, the protrusion 136 is a part of the microfluidic channel mold. In this embodiment, the capillary element 116 sits on microfluidic channel mold 144 such that the capillary channel 120 of the capillary element 116 meets the microfluidic channel mold 144 (optionally a pin can be placed on the bottom of the base mold and pushed through the microfluidic channel mold 54 similar to that shown in FIG. 5A). The mold 144 is then coated with a polymer substrate 104A (e.g., an elastic polymer) and cured. The base mold 144 is then removed and a thin membrane layer 104B is attached, thereby providing the microfluidic channel 108. Addition of control channel layer 104C then provides a desired microfluidic device 100. Alternatively, a control channel layer with the control channel on the bottom can be added, followed by sealing the "opened" control channel on a flat, preferably elastomeric, substrate. (Not shown) Depending on the thickness of the control channel layer, a solid support (not shown) can optionally be attached on the bottom of the control channel layer 104C to provide a structural integrity when the control channel 128 is actuated. Obviously, the order in which the layers are assembled, as well as the orientation of the layer comprising the control channels (e.g. "face up" or "face down") may be varied, and such permutations are contemplated. Preferably, the polymer substrate 104A, the thin membrane layer 104B, and the control channel layer 104C are comprised of a same material, thereby forming a monolithic structure.

In another embodiment, a microfluidic device and a capillary element are separately fabricated and are combined to provide an integrated microfluidic device. This method provides interchangeability of capillary elements and microfluidic devices. Integration of a separately microfabricated microfluidic device with a capillary element generally involves inserting one end of the capillary element 116 into the port 112 of the microfluidic device 100. The capillary element 116 is positioned within the port 112 such that the capillary channel 120 is in fluid communication with the microfluidic channel 108. The capillary element 116 can be removably or permanently attached to the port 112. Permanent attachment of the capillary element 116 to the port 112 can be achieved by using an adhesive material. Preferably, permanent attachment is achieved by selecting appropriate capillary element and the elastomeric polymer materials that allow formation of chemical bond between the two materials, i.e., without the use of any adhesive material.

Figure 6A:
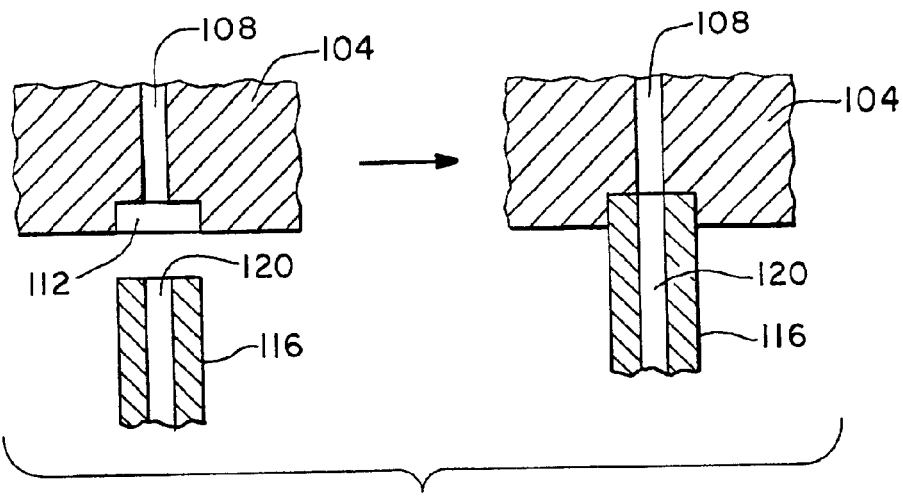
FIG. 6A is a cross-sectional view illustrating insertion of a capillary element into a port.

As stated above and shown in FIG. 6A, in one embodiment the fluid inlet/outlet comprises a capillary element 116 which extends beyond the edge of elastomeric polymer substrate 104. Preferably, the inner diameter (i.e., capillary channel 120) of capillary element 116 is substantially similar to the cross-sectional area of the microfluidic channel 108. Generally, the capillary element 116 is simply inserted into a receptacle site (i.e., port 112) and is removably attached. The capillary element 116 can also be permanently attached to the elastomeric polymer substrate 104 by using an adhesive compound or by using a capillary element which can form a bond with the elastomeric polymer substrate material. Typically, using a capillary element 116 having a cross-sectional area substantially similar, preferably slightly larger, than the cross-sectional area of the receptacle site allows formation of a hermetic seal between the capillary element 116 and the receptacle site.

Figure 6B:
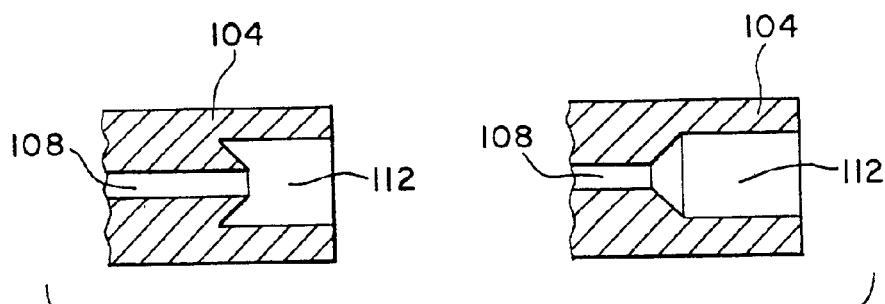
FIG. 6B is a cross-sectional view of a microfluidic device with a different port configurations for reducing the amount of dead volume.
Figure 6C:
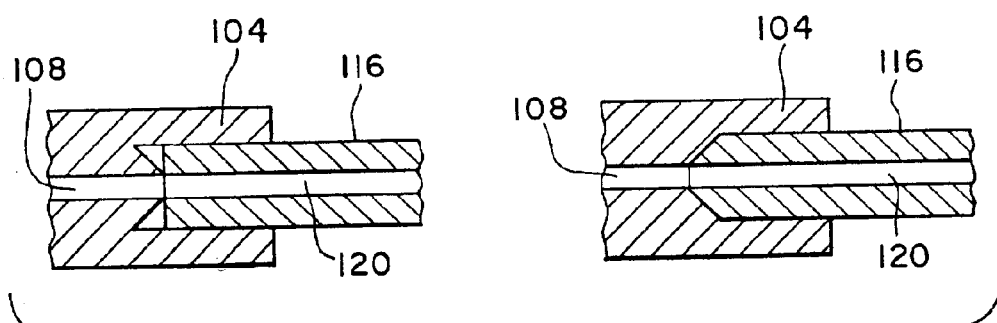
FIG. 6C is a cross-sectional view of a microfluidic device with a different port configuration and a capillary element configuration for reducing the amount of dead volume.

As with most "push fit" type of device, there is a potential for a dead volume (i.e., gap) to be present between the capillary element 116 and the microfluidic channel 108. Thus, additional features near the interface between the capillary element 116 and the microfluidic channel 108, such as those shown in FIG. 6B may be necessary to reduce the amount of potential dead volume. The amount of dead volume can also be reduced by using a tapered capillary element as shown in FIG. 6C.

The interface between the capillary element 116 and the micro fluidic channel 108 can be such that only the width (and not the height) of the microfluidic channel 108 can be increased at the interface (i.e., port 112). Alternatively, both the height and the width of the microfluidic channel 108 can be increased at the interface. While this latter interface modification provides a smaller dead volume, if the shape of the capillary element 116 and the interface is not similar, it can still result in a small yet significant dead volume. For example, capillary elements are typically cylindrical, thus if the interface area of the microfluidic device is a block shaped, then it may not provide a tight fit as desired between the capillary element 116 and the interface (i.e., port 112). Therefore, it is preferred that the shape of the interface is similar to the shape of the section of the capillary element which is inserted into the interface.

Figure 7:
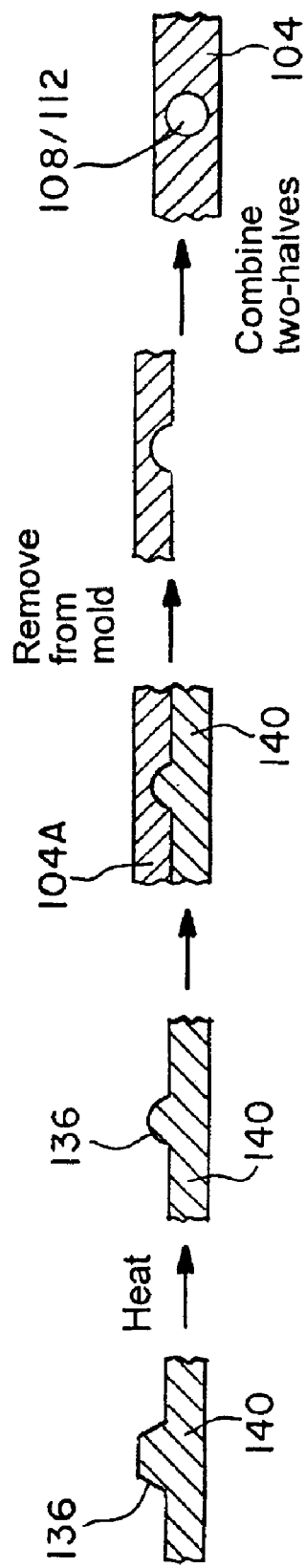
FIG. 7 illustrates a method for making a microfluidic device with a rounded microfluidic channel.

The Present inventors have found that a quasi-cylindrical interface can be prepared using the process illustrated in FIG. 7. In this manner, heating the base mold 140 produces a rounded (e.g., semi-cylindrical) protrusion 136. The elastomeric polymer precursor 104A is than coated onto this mold and cured or partially cured. Combining two layers of the cured polymer substrates produced from this mold then provides quasi-cylindrical microfluidic channels. Thus, two halves of polymer substrates are produced from two mirror image molds comprising a semi-cylindrical protrusion. When the two halves of cured or partially cured polymer substrates produced therefrom are combined and attached (i.e., bonded) together, the two combined channels form cylindrical microfluidic channels and quasi-cylindrical capillary element interfaces (i.e., port 112).

Figure 8A:
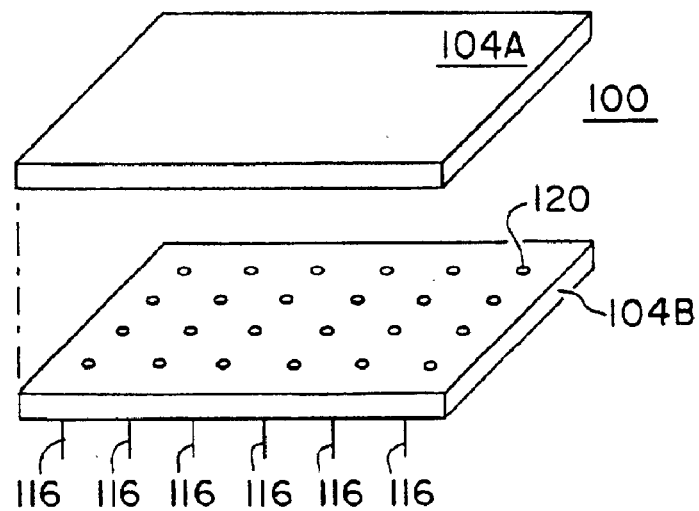
FIGS. 8A and 8B shows microfluidic devices comprising a plurality of capillary elements or fluid inlet/outlet systems.
Figure 8B:
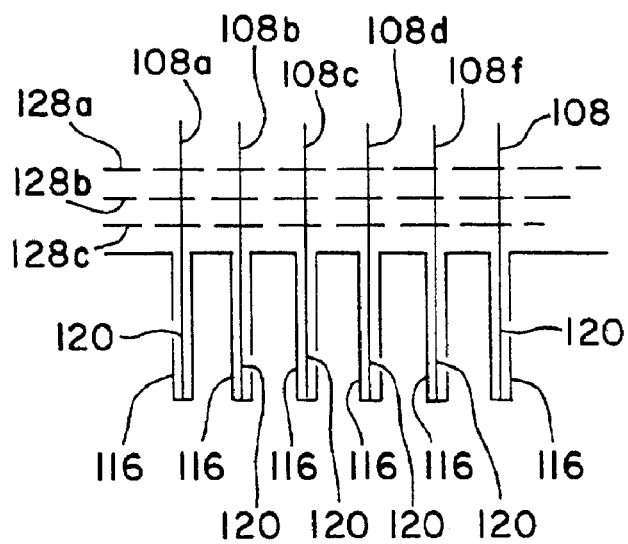

Microfluidic devices of the present invention can comprise a plurality of any of the elements described herein. For example, as shown in FIGS. 8A and 8B, microfluidic device 100 can comprise a plurality of capillary elements 116. This allows sampling of a large number of fluid samples simultaneously. The presence of a plurality of capillary elements is particularly useful in biological or chemical assays. Microfluidic devices having an array of capillary elements can be fabricated using any of the methods disclosed herein or known to one skilled in the art. One particular process for producing a microfluidic device comprising a plurality of capillary elements is illustrated in FIG. 8A. In this embodiment, an elastomeric layer 104A comprising microfluidic channel (not shown in FIG. 8A) is separately microfabricated and is attached to a base layer 104B which comprises a plurality of capillary elements disposed therethrough. The base layer 104B can be an elastomeric or non-elastomeric layer.

Figure 9:
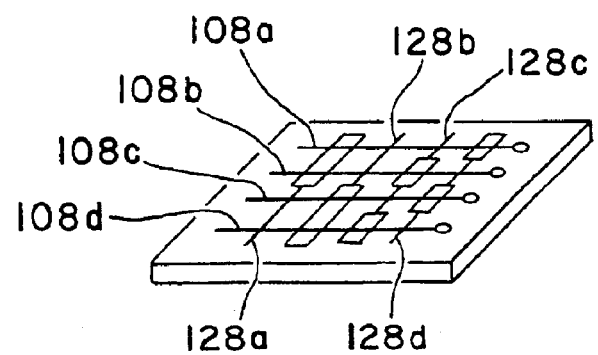
FIG. 9 is a schematic drawing of control channel and microfluidic channel configuration illustrating a selective fluid control within microfluidic channels.

Each capillary element 116 in FIGS. 8A and 8B has at least one corresponding microfluidic channel that is in fluid communication. As schematically illustrated in FIG. 8B, microfluidic device 100 having a plurality of microfluidic channels 108a–108f can be used to dispense or inject a plurality of fluid samples simultaneously. FIG. 8B shows a single peristaltic pump (comprised of control channels 128a, 128b and 128c) that controls all of the microfluidic channels. Alternatively, a separate peristaltic pump for each microfluidic channels can be provided as illustrated in FIG. 9. In FIG. 9, the rectangular box represents pump or a flow control system for moving the fluid within the microfluidic channel. Thus, in FIG. 9, control channel 128a controls the fluid flow within microfluidic channels 108a and 108b, control channel 128b controls the fluid flow within microfluidic channels 108c and 108d, control channel 128c controls the fluid flow within microfluididc channels 108b and 108d, and control channel 128d controls the fluid flow within microfluidic channels 108a and 108c.

Alternatively, a separate peristaltic pump for each microfluidic channels can be provided as illustrated in FIG. 9. In FIG. 9, the rectangular box represents a flow control system to control the amount of liquid being sipped. Liquid can be selectively drawn into the microfluidic device by activating the appropriate control lines, resulting in closure of the appropriate valves. For example, in FIG. 9, the transport of liquid is controlled in a multiplexing scheme. Fluid flow in channel 108a can be enabled while disabling 108b–c by activating control lines 128b and 128c, thus closing the appropriate valves. In this way, sipping and dispensing can be controlled by the use of valves.

Figure 3D:
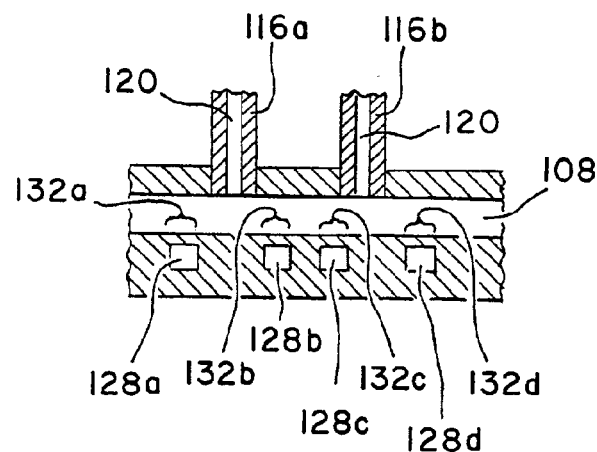
FIG. 3D is a cross-sectional view of a microfluidic device comprising a plurality of capillary elements and a plurality of control channels.

As shown in FIG. 3D, when a plurality of capillary elements are used, control channel 128a–d, located within the polymer substrate 104, can be used to selectively allow introduction of a desired fluid into the microfluidic channel 108. The control channels 128a–d are separated from the microfluidic channel 108 by thin elastic membranes 132, which are typically composed of the same polymer substrate material. Alternatively, introduction of each fluid samples can be controlled by selectively occluding the capillary element (e.g., 116a or 116b in FIG. 3D). When control channel 128b is actuated, capillary element 116a is in fluid communication with the left segment, but not the right segment, of flow channel 108; if control channel 128a is also actuated, the capillary element is isolated and is not in fluid communication with the left or right segments of flow channel 108.

VIII. Exemplary Fluid Sampling/Dispensing Microfluidic Devices

One particular embodiment of the present invention is illustrated in FIGS. 2A and 2B. In this embodiment, the fluid is introduced into the microfluidic channel 108 (not shown in FIGS. 2A and 2B) by placing the capillary element 116 into a vessel 50 containing the fluid 54. In FIG. 2A, the fluid is drawn into the microfluidic channel by using an external fluid transporting device (e.g., vacuum) 124. In FIG. 2B, the fluid is drawn into the microfluidic channel by sealing the vessel 50 with a seal 58 and increasing the pressure within the vessel 50 using an external device 124, e.g., pressurizing device. It should be appreciated that using a pressurizing device instead of a vacuum in FIG. 2A or using a vacuum instead of a pressurizing device in FIG. 2B allows withdrawal (i.e., dispensing) of the fluid from the microfluidic channel. In such instances, however, the capillary element 116 is typically above the fluid level in the vessel 50 (if any fluid is present).

Alternatively, and preferably, the fluid transporting means comprises at least one control channel 128. For example, as illustrated in FIGS. 3B–3C, one or more control channels 128 act as a peristaltic pump 148 to transport the fluid to and from the microfluidic channel 108. By adjusting the frequency and/or the volume of control channels 128a–c, which make-up a peristaltic pump 148, a precise amount of fluid can be sampled or dispensed.

The fluid is introduced into the microfluidic channel 108 by immersing the capillary element 116 in a fluid medium and activating the peristaltic pump 148 which comprises at least one control channel 128. The peristaltic pump 148 can comprise a plurality of control channels as shown in FIG. 3C. Such a peristaltic pump requires actuation of each control channel independently. The amount of fluid transported depends on the frequency of the control channel actuation as well as the amount of fluid volume transported per actuation. In addition, use of a plurality of control channels allows the peristaltic pump 148 to transport a fluid in either direction depending on the sequence of each control channel actuation.

Depending on the velocity of fluid dispensing and the material of the elastomeric polymer substrate 104, the configuration of the port 112, the presence or absence of a capillary element, as well as other factors, the fluid that is dispensed from the microfluidic device 100 can form a droplet. One can decrease this droplet formation by dispensing the fluid in a jet-spray like manner (as discussed in detail below) or by configuring the shape of the elastomeric polymer substrate 104 near the fluid outlet. For example, by providing a sharply-tipped fluid outlet (i.e., port 112), as shown in FIG. 11A, one can reduce droplet size and minimize droplet-microfluidic device contact. Additionally (or alternatively) the outside surface of the polymer substrate near the fluid outlet can be coated with (or made from) a material which repels the fluid. For example, if an aqueous fluid is used with the microfluidic device 100, one can use a hydrophobic material for the polymer substrate or coat the surface near the fluid outlet with a hydrophobic material. Conversely, if a relatively non-polar organic fluid is used, one can use a hydrophilic material for the polymer substrate or coat the surface near the fluid outlet with a hydrophilic material. This "opposite polarity" between the fluid and the material near the fluid outlet decreases droplet size and droplet-microfluidic device contact. Such decrease can be due to reduction in the surface tension between the fluid and the microfluidic device. If a capillary element is present, it can be made from such a material.

By adjusting the fluid outlet portion (e.g., port 112 or a capillary element 116) of the microfluidic channel 108, the microfluidic device 100 can be configured to be a jet-spray type dispensing device. For example, one can increase the velocity of fluid ejection relative to its velocity within the microfluidic device 100 by tapering the microfluidic channel 108 near the outlet port of the microfluidic device 100 (see for example, FIGS. 11B and 11C). In FIGS. 11B and 11C, the peristaltic pump 148 can be any of the configurations discussed above. As the fluid is pushed along the microfluidic channel 108, it experiences an increased velocity at the narrower section of microfluidic channel 108, thereby resulting in a jet-spray like dispensing of the fluid.

Another aspect of the present invention provides a fluid dispensing microfluidic device which can dispense a precise amount of fluid. One such embodiment is schematically illustrated with control channels 128 and microfluidic channel 108 in FIG. 12A. In this embodiment, a fluid is introduced into the microfluidic channels 108 from the direction $108a_2$ using any of the above described methods or conventional fluid introducing methods. The microfluidic channel 108 is partially closed using control channels $128a_1$ and $128a_4$ so that the fluid travels in the direction from $108a_2$ to $108a_3$, as shown in FIG. 12B (X indicates closed control channel). Thereafter, all microfluidic channels are closed by actuating control channels $128a_1-128a_4$, as shown in FIG. 12C. At this stage, the volume of fluid contained in the closed microfluidic channel is the volume defined by the microfluidic channel 108 of length from control channel $128a_1$ to control channel $128a_4$. By selectively opening the control channels $128a_1$ and $128a_4$ and flushing the microfluidic channel 108 in the direction from $108a_1$ to $108a_4$ using a fluid transporting means, the precise amount of fluid is dispensed through the fluid outlet (see FIG. 12D). Dispensing of the fluid can be driven by pressure, e.g., from a gas or a liquid that is introduced from $108a_1$, or by suction, e.g. from a vacuum introduced from $108a4$, or it can be driven by a pump, such as a peristaltic pump discussed above.

Figure 12E:
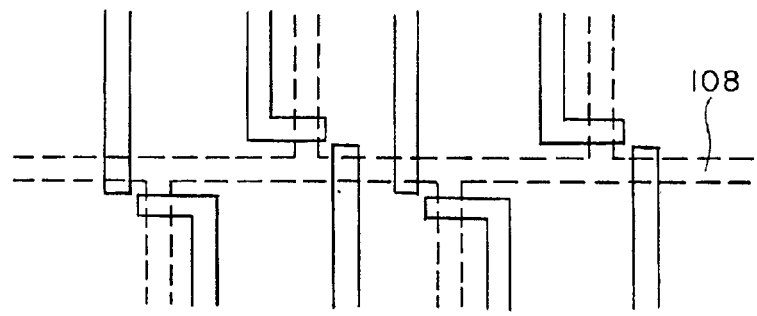
FIGS. 12E–12F illustrate a series of microfluidic channel and control channel configurations and their use for mixing fluid samples of fixed quantities.
Figure 12F:
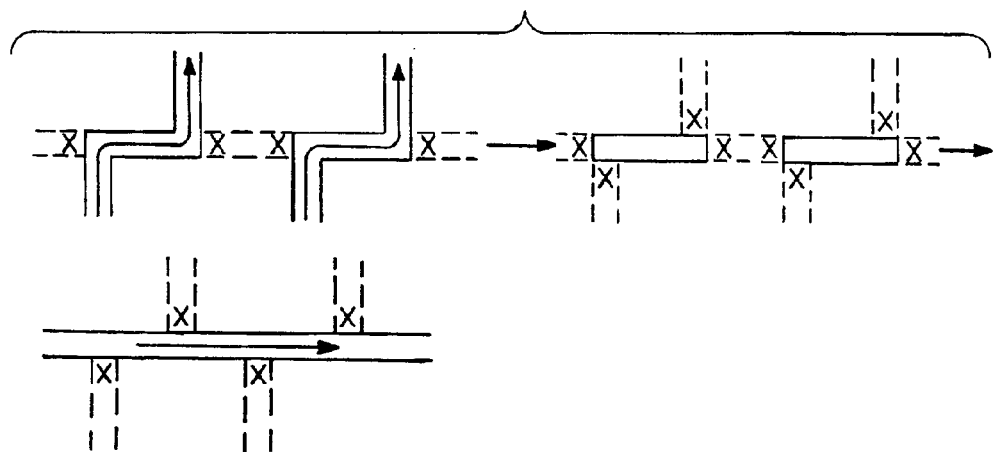
Figure 12G:
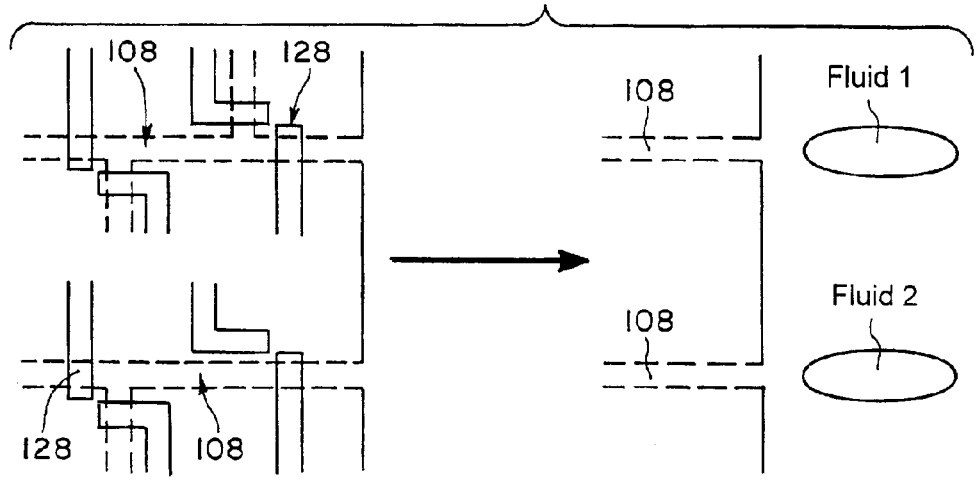
FIG. 12G illustrates parallel configuration of microfluidic channels and control channels and their use for dispensing multiple fluid samples simultaneously or sequentially.

One can also have a plurality of such channel configurations arranged in series, as illustrated in FIG. 12E–12F, to allow mixing of a plurality of known quantities of fluid samples. In addition, one can have a plurality of microfluidic channels in parallel, as illustrated in FIG. 12G, to simultaneously (or sequentially depending on the order of control channel actuation) dispense a plurality of fluids from a single microfluidic device 100.

Figure 13A:
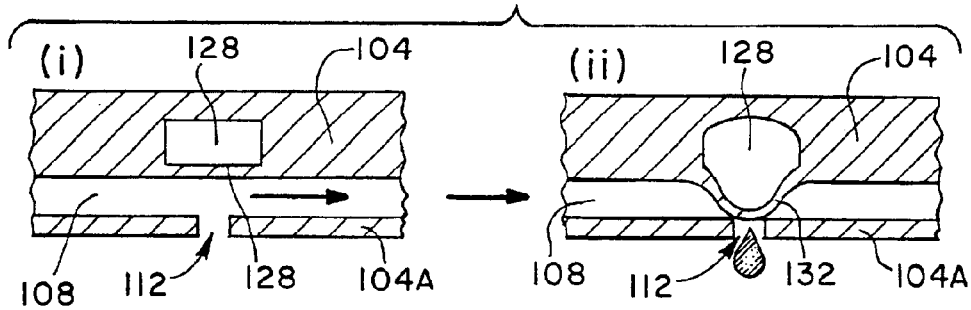
FIG. 13A is an illustration of vertical fluid dispensing microfluidic device.
Figure 13B:
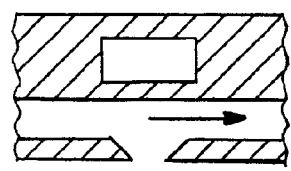
FIG. 13B is an illustration of a microfluidic channel having a tapered vertical port.

Another aspect of the present invention provides a fluid dispensing microfluidic device in which a droplet of fluid is dispensed through a vertical opening (i.e. a via or passageway). As used herein the term "vertical" refers to a direction which is substantially perpendicular to the direction of the fluid flow immediately above the vertical opening. Usually, this is perpendicular to the plane of the microfluidic device. One particular embodiment of this aspect of the invention is illustrated in FIG. 13A. Typically, the fluid travels through the microfluidic channel 108 in the direction shown by the arrow in FIG. 13A(i). Due to a capillary action and/or other forces, e.g., surface tension, the fluid typically does not flow down the vertical port 112. When the fluid dispensing control channel 128 is actuated as shown in FIG. 13A(ii), the thin elastic membrane 132 deflects downward and pushes the fluid sample through the vertical fluid port 112. The base layer 104A can be an elastic material such as the microfluidic device substrate 104 material, or it can be a solid material such as glass, silicon wafer, quartz, metal plate, and the like. By rapidly actuating the fluid dispensing control channel 128, one can dispense a stream of fluid droplets through the vertical fluid port 112. Alternatively, the flow of fluid through the microfluidic channel 108 can be stopped prior to dispensing the fluid by closing two control channels (not shown) located on both sides of the fluid dispensing control channel 128. The vertical fluid port 112 can be tapered as shown in FIG. 13B to provide a better seal with the thin elastic membrane 132 when the fluid dispensing control channel 128 is actuated.

Another aspect of the present invention provides a fluid sample diluting microfluidic device. One such embodiment includes microfluidic channel and control channel configurations shown in the above described FIGS. 12A–12G. For example, after a fluid sample is placed within the area between the control channel $128a_1$ and $128a_4$ as shown in FIG. 12C, one can introduce a diluting solvent through the microfluidic channel $108a_1$ (see FIG. 12A). In this manner, the fluid sample and the diluting solvent exiting through the microfluidic channel $108a_4$ becomes admixed. The section $108a_4$ of microfluidic channel can include a reservoir section (not shown) which has larger volume than the microfluidic channel 108 or a rotary pump (i.e., a fluid circulating section, not shown) to allow mixing of the fluid sample and the diluting solvent prior to being dispensed from the microfluidic device 100 or prior to being transferred to other areas of the microfluidic device 100.

Figure 14A:
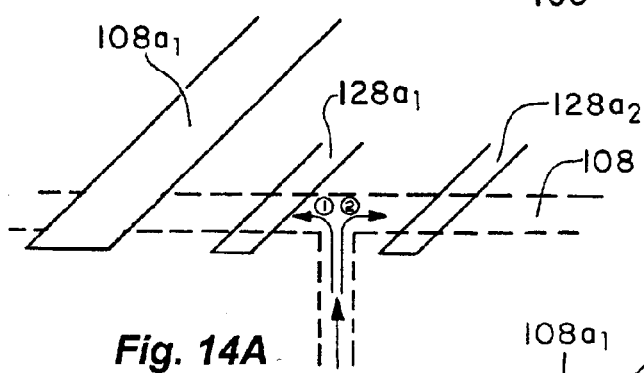
FIG. 14A is a schematic illustration of microfluidic channel and control channel configuration which can be used for sorting and/or diluting samples.
Figure 14B:
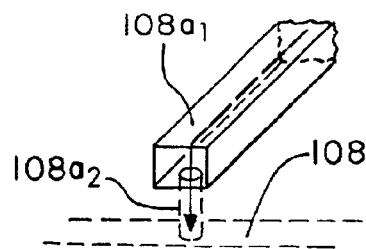
FIG. 14B is a close-up illustration showing interconnection between two microfluidic channels which can be used to dilute a sample.

Another embodiment of the present invention comprises microfluidic devices with control channel and microfluidic channel configuration shown in FIG. 14A. In this embodiment, the fluid sample flow direction is controlled by control valves $128a_1$ and $128a_2$. For example, when control channel $128a_1$ is actuated, the fluid flow in the direction indicated by the arrow (2) and when control channel $128a_2$ is actuated, the fluid flow in the direction indicated by the arrow (1). This selection of fluid flow direction can be made based on detection of a particular sample (not shown) as described in, for example, U.S. patent application Ser. No. 08/932,774, filed Sep. 25, 1997, and U.S. Provisional Patent Application Serial Nos. 60/108,894, filed Nov. 17, 1998 and 60/806,394, filed May 22, 1999, all of which are incorporated herein by reference in their entirety. Thus, when a desired sample is detected, control channel $128a_2$ is actuated to change the direction of fluid flow from the arrow direction (2) to (1). Simultaneously, a diluting solvent (e.g., a buffer solution or a nutrient medium) can be added through the microfluidic channel $108a_1$. The microfluidic channel $108a_1$ is located above but is in a fluid communication with the microfluidic channel 108 through a connecting microfluidic channel 108$a_2$ as shown in FIG. 14B.

Figure 15A:
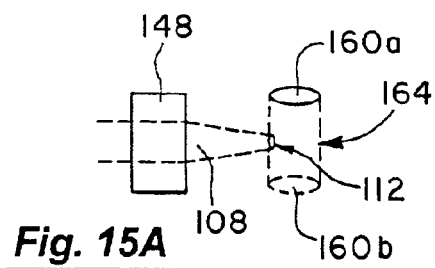
FIGS. 15A and 15B are schematic illustrations of a microfluidic device where the port is located within an interstitial space of a body structure.
Figure 15B:
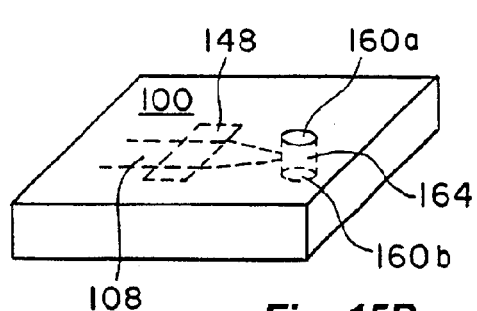

Yet another embodiment for diluting a fluid sample comprises a microfluidic device such as that illustrated in FIGS. 15A and 15B. In this embodiment, the port 112 which dispenses the fluid from the microfluidic channel 108 is located within a passageway 164. The passageway 164 is typically a bore and defines an interstitial surface within the body structure and extends from one surface 160$a$ to another surface 160$b$ of the microfluidic device 100. When the fluid is introduced into the passageway 164 from the microfluidic channel 108, for example, by a peristaltic pump 148, the fluid is suspended within the passageway 164 by capillary action and/or other static forces, such as surface tension. The fluid sample within the passageway 164 can then be flushed away from the microfluidic device 100 by adding a rinsing fluid into the opening 160$a$. The rinsed fluid then exits through the opening 160$b$ and can be collected if desired.

When a peristaltic pump comprises a plurality of control channels (i.e., control lines), each control channel is separately or sequentially addressable. Therefore, peristalsis can be actuated by the pattern of actuating one or more control channels together.

Use of control channel(s) 128, in microfluidic devices of the present invention allows fine control over a very small fluid sample manipulation. For example, in one particular embodiment, microfluidic devices of the present invention are capable of achieving a fluid flow rate of about 0.02 $\mu$L/min or less. Preferably, microfluidic devices of the present invention can achieve a fluid flow rate of about 0.5 $\mu$L/min or less and more preferably 1 $\mu$L/min or less.

In addition, unlike conventional microfluidic devices, microfluidic devices of the present invention can achieve such a small fluid flow rate with great accuracy. For example, microfluidic devices of the present invention can achieve 0.02 $\mu$L/min flow rate within about at least 90% accuracy, preferably within about at least 95% accuracy, and more preferably within about at least 99% accuracy.

Additional objects, advantages, and novel features of this invention will become apparent to those skilled in the art upon examination of the following examples thereof, which are not intended to be limiting.

EXAMPLES

Example 1

This example illustrates a three-layer fabrication process for producing a microfluidic sipper.

Three silicon wafers were cleaned by washing with acetone, isopropyl alcohol (IPA), deionized (DI) water, IPA and drying with $N_2$. The resulting wafers were dehydration baked on a hot plate at 100° C. for 5 minutes, cooled and treated with hexamethyldisilazane (HMDS) vapor for 10 minutes in a chamber. The wafers were then removed from the HMDS vapor chamber and spin coated with Shipley 5740 resist to produce a 10 $\mu$m layer. The resulting wafers were softbaked in a 90° C. oven for 1 hr, exposed to UV and developed in Shipley 2401 developer. The developed wafers were hard baked in a 150° C. oven for 1 hr to provide a rounded profile photoresist mold.

The molds were used to make the sipping device using a two component silicone rubber (GE RTV 615). The control layer, i.e., layer comprising the control channels, was made by mixing a 4:1 ratio of A:B components to produce a 4 mm thick layer. The fluid layer, i.e., layer comprising one or more microfluidic channel, was made using a 30:1 ratio of A:B components and spun on the wafer to produce a 76 $\mu$m layer. The sipping layer, i.e., third layer, was made using a 4:1 ratio of A:B components and spun on the wafer to produce a 76 $\mu$m layer. The three layers were then baked in an oven for an initial cure. The control layer was baked for 1.5 hours, the fluid layer was baked for 45 minutes, and the sipping layer was baked for 45 minutes. A 10:1 mixture of A:B is made after the initial sipping layer bake and poured on to the sipping layer to provide a 2 mm thick layer. This layer is then baked for an additional 45 minutes. After these bakes, vias are punched for the control layer and it was aligned on top of the fluid layer. They were then baked for 15 minutes to bond the control and fluid layers. Vias to access the fluid layer were then punched in this bonded layer. Vias were punched in the sipping layer. The control/fluid layer was then aligned to the sipping layer in face to face bonding and baked for 1.5 hours. After this final bake, capillary tubes were inserted into the sipping layer to complete the microfluidic device. The sipping layer punches were made smaller than the outer diameter of the capillary tube, thus ensuring a secure seal.

Example 2

This example illustrates a three-layer fabrication process for producing a microfluidic dispenser.

Two silicon wafers were cleaned by washing with acetone, IPA, DI water, IPA and drying with $N_2$. The wafers were then dehydration baked on a hot plate at 100° C. for 5 minutes, cooled and treated with HMDS vapor for 10 minutes. The wafers were removed from the HMDS vapor chamber and coated with Shipley 5740 resist spun to produce a 7 $\mu$m layer. The wafers were then softbaked in a 90° C. oven for 1 hr, exposed with UV and developed in Shipley 2401 developer. The developed wafers were hard baked on a 200° C. hotplate for 1 hr, cooled and placed in a HMDS vapor chamber for 10 minutes. AZ PLP 100XT resist was spun on the wafers to produce a 45 $\mu$m layer. The wafers were then soft baked at 90° C. for 1.5 hrs, cooled, exposed to UV, developed in AZ 400K developer and at 200° C.

The two layer portion of the PDMS chip was made using the process described in Science 7 April 2000, Volume 288 pp. 113–116 "Monolithic Microfabricated Valves and Pumps by Multilayer Soft Lithography" using GE RTV 615 silicone polymer.

The control layer was made by mixing a 4:1 ratio of A:B components and the fluid layer was made using a 30:1 ratio of A:B components. The control layer was 4 mm thick and the fluid layer was spun to produce a 76 $\mu$m thick layer. The two layers were baked for 1.5 hrs at 80° C. for the initial cure. After the initial cure, the dies are cut and vias are punched to the control channel. The control layer was then aligned on top of the fluid layer and the chip was baked for 1.5 hrs at 80° C. The vias were punched to the fluid layer after the bake and the chip was ready to be sealed. The chip was bonded to a final 4:1 ratio of A:B, which was 76 $\mu$m thick, using oxygen plasma treatment. The final chip was placed in a 80° C. oven for 15 minutes to bond the final layers together. The outlet via was punched through the entire chip and was placed on a glass slide, making a device with a flow-through via similar to that schematically illustrated in FIG. 15A–B.

Example 3

This example illustrates a microfabrication process for producing a microfluidic dispenser containing a single line pump, i.e., one control channel peristaltic pump.

Two silicon wafers were cleaned by washing with acetone, IPA, DI water, IPA and drying with $N_2$. The wafers were then dehydration baked on a hot plate at 100° C. for 5 minutes, cooled, treated with HMDS vapor and coated with AZ 5214-E resist spun to produce a 2 μm layer. The wafers were then softbaked on a 100° C. hotplate for 2 min, exposed to UV, developed in AZ 400K developer and hard baked on a 200° C. hotplate for a 1 hr. The wafers were cooled and treated with HMDS vapor for 10 minutes. AZ PLP 100XT resist was spun on to the wafers to produce a 45 μm layer. The wafer were then soft baked at 90° C. for 1.5 hrs, exposed to UV, developed in AZ 400K developer and hard-baked at 200° C.

The molds were then used to make a microfluidic device comprising a single control channel peristaltic pump using a two component silicone rubber (GE RTV 615). The control layer was made by mixing a 10:1 ratio of A:B components to produce a 4 mm thick layer. The fluid layer was also made using a 10:1 ratio of A:B components and spun on the wafer at 2500 RPM. The two layers were then baked in an 80° C. oven for an initial cure. Both of the layers were baked for 1.5 hours. The control layer was then baked an additional 45 minutes at 120° C. while the fluid layer was baked for an additional 45 minutes in the 80° C. oven. The vias were punched in the control layer and the two layers were treated with $O_2$ plasma for 30 seconds. The two layers were then aligned and baked in an 80° C. oven for 15 minutes. Vias were punched to the fluid layer to produce a microfluidic device comprising a single control channel peristaltic pump.

Example 4

Figure 16:
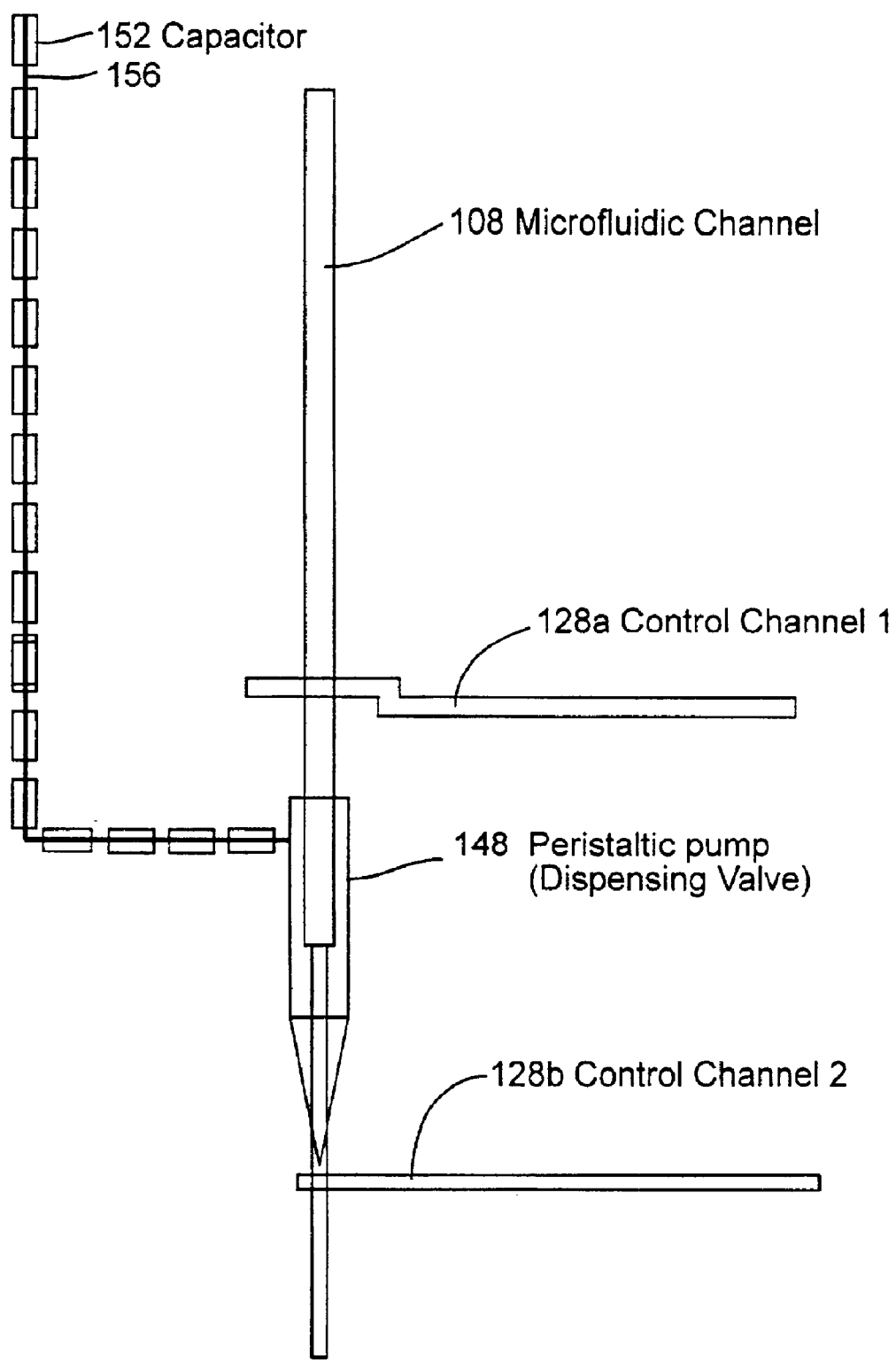
FIG. 16 is a schematic illustration of a microfluidic device comprising a single control channel pump having a plurality of capacitors.

This Example illustrates the mode of use of a Single Control Channel Pump (Dispenser):

The microfluidic device which is schematically illustrated in FIG. 16 functions by closing a middle valve (control channel 128a). First, a valve (i.e., control channel 128a) at the inlet end of the dispensing valve is closed to isolate the fluid in the channel. Second, the dispense valve (i.e., pump 148) is closed to dispense the desired fluid volume. A closed inlet valve 128a prevents flow of the fluid in the wrong direction. The valve, i.e., control channel 128b, at the outlet of the dispense valve is then closed to prevent backflow of the fluid. After the fluid has been dispensed, the inlet valve 128a, the pump 148, and the outlet valve 128b are opened and the dispenser is ready to cycle again.

The microfluidic device in FIG. 16 includes a tapered microfluidic channel 108, which is 45 μm high. This tapering allows the valve (i.e., pump 148) to close from the wide section to the narrow section of the microfluidic channel 108. This section tapers from a width of 350 μm to 200 μm. The input line leading to the pump 148 (control channel 128) varies in cross section, i.e., the input line to the pump 148 comprises a plurality of capacitors 152 which are interdispersed by narrower channels 156. The presence of capacitors 152 allows the pump 148 to fill slowly. The narrow cross sections are 50 μm×7 μm and the thick cross sections are 300 μm×45 μm. The tip of the pump 148 narrows at the end to allow a more full and complete actuation of the pump. The pump 148 is activated when it is actuated, e.g., when pressure is applied to the control line. The volume of the fluid located under the pump 148 is dispensed within the chip or external to the chip.

Example 5

This example illustrates the mode of use of a peristaltic pump comprising a plurality of control channels.

Figure 17:
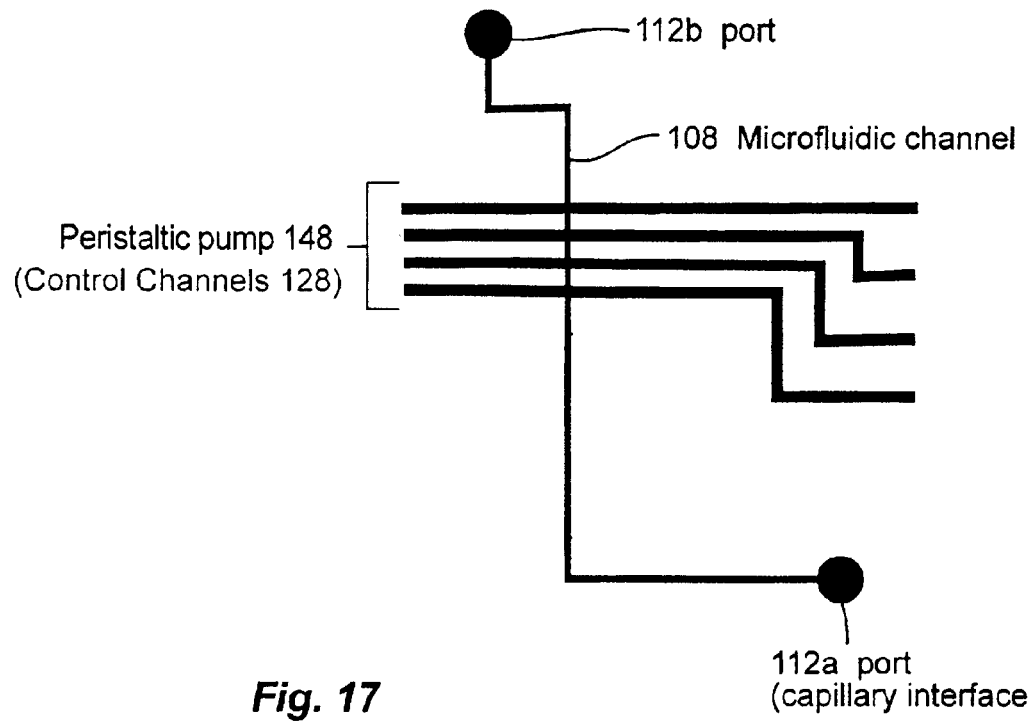
FIG. 17 is a schematic illustration of a microfluidic device having a peristaltic pump comprising a plurality of control channels.

A microfluidic device comprising a plurality of control channels which act as a peristaltic pump is schematically illustrated in FIG. 17, which can be a three layer device that has a capillary interface, i.e., port 112a. Microfluidic devices of this configuration can sample or dispense the fluid depending on a particular actuation sequence of control channels 128. For example, when the control channels 128 are actuated in a 001, 010, 100 sequence, i.e., from bottom to top in FIG. 17, a fluid is drawn into the microfluidic channel 108 from the external source via the capillary element which can be present in the port 112a. The microfluidic channels 108 for this device are 100 μm wide and 10 μm high. The control lines 128 are 200 μm wide and 10 μm high. The peristaltic pump action caused by this control sequence draws the fluid into the microfluidic channel 108.

Alternatively, the fluid can be introduced into the microfluidic channel 108 by using a vacuum source attached to the fluid line at the port 112b.

Example 6

This example illustrates the mode of use of a peristaltic pump comprising a single line control channels.

Figure 18:
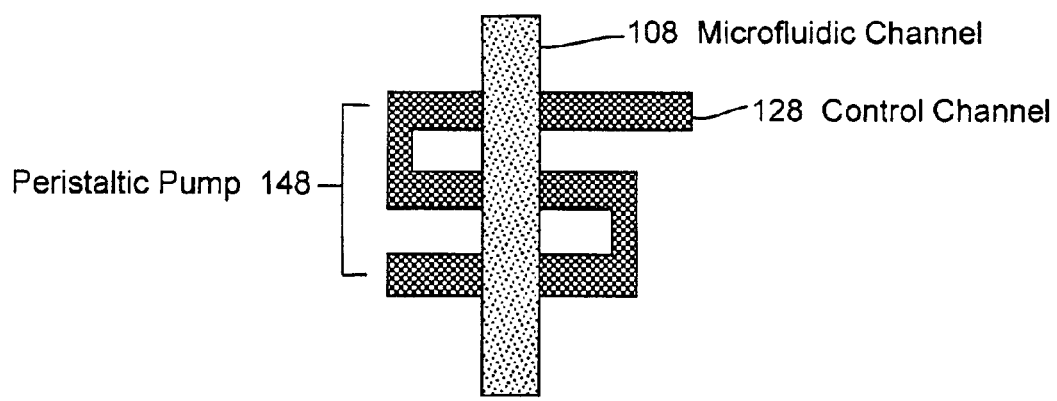
FIG. 18 is a schematic illustration of a microfluidic device having a peristaltic pump which comprises a single control channel.

A single line peristaltic pump is a pump which uses a single control line, compared to two or more, preferably three, control channels that are typically used. See FIG. 18. By varying the cross sectional area of the control channel region, a time delay for filling the three chambers can be created. The cross section of the thick regions (i.e., areas of larger cross-section) is typically at least about 10 times greater than the cross section of the thinner regions (i.e., areas of smaller cross-section). Preferably, the cross-section of the thick regions is from about 10 times to about 1000 times greater than the cross-section of the thinner regions, more preferably from about 100 times to about 500 times, and still more preferably from about 200 times to about 300 times. For example, when the cross-section of the thick regions is 20×100 microns, the cross section of the thinner sections is 2×5 microns.

When a capacitor is used to provide a delay in filling the pump, the cross-section area of the capacitor 152 is generally at least about 35 times greater than the cross-section area of the channel 156 leading to the control channel 128, preferably at least about 10 times to about 500 times greater, and more preferably at least about 30 times to about 100 times greater.

UTILITY

A method for introducing and dispensing fluid into microfluidic devices is essential in nearly every application that microfluidic devices will be used. These can include, but is not limited to, biotechnology, analytical, and medical applications. Fluid dispensing is required in a multitude of biotechnology applications, such as high throughput screening. The dispenser device can be used to eject fluid directly into a well plate for mixing reagents and analysis. In a variation of this, the dispenser could also dispense a specified volume to a flush channel within the microfluidic device and then ejected into a well plate. Another application for dispensing is mass spectrometry. The microfluidic dispenser would be capable of ejecting droplets of fluid into the mass spectrometer for analysis. The dispenser could also be used to dispense a specified volume of liquid, which could contain test specimen or reagants, to the edge of the device and then transferred to a plate by contact for analysis. The dispenser could also be used for medical applications such as drug delivery. Such a device could be used to eject a precise volume of liquid in specified time intervals. The dispenser could perhaps even be a device that can be implanted into the body to dispense medication or nutrients.

The ability to introduce liquid is necessary for any application which will require the transfer of liquid from a medium to the microfluidic device. One example of this is high throughput screening analysis. A method of introducing sample into the microfluidic device is required with the current use of well plates. The capillary interface can be inserted into the liquid well and liquid drawn into the microfluidic device through the use of external vacuum or peristaltic pumping. This type of interface would enable automation of the microfluidic device with current technology. The ability to introduce liquid would also be useful in applications where direct contact with the test sample is not desired or feasible. An example of this would be use of the sipper could be for drawing blood into the microfluidic device for anaylsis.

While the present invention has been described herein with reference to particular embodiments thereof, a latitude of modification, various changes and substitutions are intended in the foregoing disclosure. It will be appreciated that in some instances some features of the invention will be employed without a corresponding use of other features without departing from the scope of the invention as set forth herein. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention shall include all embodiments and equivalents falling within the scope of the appended claims.

What is claimed is:

1. A microfluidic device comprising:
   a body structure comprising an elastomeric polymer substrate;
   a microfluidic channel disposed within said elastomeric polymer substrate;
   a port on a surface of said body structure and in fluid communication with said microfluidic channel for introducing or dispensing a fluid to or from said microfluidic channel;
   a means for transporting the fluid to and from said microfluidic channel; and
   at least one valve system which comprises:
      a control channel disposed within said elastomeric polymer substrate; and
      one or more valves operatively connected to said microfluidic channel to regulate fluid flow through said microfluidic channel, wherein each of said valves comprises a portion of said elastomeric polymer substrate that is located between said control channel and said microfluidic channel, and wherein each of said valves is capable of being deflected into or retractable from said microfluidic channel upon which said valve operates in response to an actuation force applied to said valve, said valve when positioned in said microfluidic channel is capable of affecting fluid flow therethrough, wherein:

said means for transporting the fluid comprises a fluid pump comprising at least one of said valve system;

said fluid pump comprises a single control channel; and said fluid pump control channel further comprises at least one capacitor which is capable of delaying actuation of said control channel.

2. A microfluidic device comprising:
   (a) a body structure comprising an elastomeric polymer substrate;
   (b) a microfluidic channel disposed within said elastomeric polymer substrate;
   (c) a fluid inlet in fluid communication with said microfluidic channel; and
   (d) a fluid pump for introducing or dispensing a fluid to or from said microfluidic channel through said port, wherein said fluid pump comprises:
      (i) a fluid pump control channel disposed within said elastomeric polymer substrate; and
      (ii) one or more pump valves operatively connected to said microfluidic channel to regulate fluid flow through said microfluidic channel, wherein each of said pump valves comprises a portion of said elastomeric polymer substrate that is located between said fluid pump control channel and said microfluidic channel, and wherein each of said pump valves is capable of being deflected into or retractable from said microfluidic channel upon which said fluid pump valve operates in response to an actuation force applied to said fluid pump control channel, said fluid pump valve when positioned in said microfluidic channel is capable of affecting fluid flow therethrough, wherein:

said fluid pump comprises one fluid pump channel; and said fluid pump channel comprises a plurality of capacitors which are capable of delaying actuation of said fluid pump control channel.

* * * * *